US008142778B2

(12) United States Patent
Davis et al.

(10) Patent No.: US 8,142,778 B2
(45) Date of Patent: *Mar. 27, 2012

(54) METHODS OF TREATMENT USING CTLA-4 ANTIBODIES

(75) Inventors: Thomas Andrew Davis, Clarksville, MD (US); Tibor P. Keler, Princeton, NJ (US); Robert F. Graziano, Princeton, NJ (US); Alan J. Korman, Piedmont, CA (US)

(73) Assignee: Medarex, Inc., Princeton, NJ (US)

( * ) Notice: Subject to any disclaimer, the term of this patent is extended or adjusted under 35 U.S.C. 154(b) by 212 days.

This patent is subject to a terminal disclaimer.

(21) Appl. No.: 12/246,791

(22) Filed: Oct. 7, 2008

(65) Prior Publication Data

US 2009/0117037 A1  May 7, 2009

Related U.S. Application Data

(63) Continuation of application No. 10/411,973, filed on Apr. 11, 2003, now Pat. No. 7,452,535.

(60) Provisional application No. 60/372,284, filed on Apr. 12, 2002, provisional application No. 60/381,274, filed on May 17, 2002.

(51) Int. Cl.
    *A61K 39/395* (2006.01)
(52) U.S. Cl. .................................... 424/130.1
(58) Field of Classification Search .............. None
    See application file for complete search history.

(56) References Cited

U.S. PATENT DOCUMENTS

| 4,399,216 | A | 8/1983  | Axel et al.      |
| 4,681,581 | A | 7/1987  | Coates           |
| 4,683,195 | A | 7/1987  | Mullis et al.    |
| 4,683,202 | A | 7/1987  | Mullis           |
| 4,735,210 | A | 4/1988  | Goldenberg       |
| 4,740,461 | A | 4/1988  | Kaufman          |
| 4,816,397 | A | 3/1989  | Boss et al.      |
| 4,921,040 | A | 5/1990  | Ueruenduel et al.|
| 4,959,455 | A | 9/1990  | Clark et al.     |
| 5,101,827 | A | 4/1992  | Goldenberg       |
| 5,151,510 | A | 9/1992  | Stec et al.      |
| 5,194,594 | A | 3/1993  | Khawli et al.    |
| 5,434,131 | A | 7/1995  | Linsley et al.   |
| 5,530,101 | A | 6/1996  | Queen et al.     |
| 5,545,806 | A | 8/1996  | Lonberg et al.   |
| 5,545,807 | A | 8/1996  | Surani et al.    |
| 5,556,763 | A | 9/1996  | Ochoa et al.     |
| 5,569,825 | A | 10/1996 | Lonberg et al.   |
| 5,585,089 | A | 12/1996 | Queen et al.     |
| 5,591,669 | A | 1/1997  | Krimpenfort et al.|
| 5,612,205 | A | 3/1997  | Kay et al.       |
| 5,625,126 | A | 4/1997  | Lonberg et al.   |
| RE35,500  | E | 5/1997  | Rhodes           |
| 5,633,425 | A | 5/1997  | Lonberg et al.   |
| 5,643,763 | A | 7/1997  | Dunn et al.      |
| 5,648,471 | A | 7/1997  | Buttram et al.   |
| 5,656,272 | A | 8/1997  | Le et al.        |
| 5,661,016 | A | 8/1997  | Lonberg et al.   |
| 5,693,761 | A | 12/1997 | Queen et al.     |
| 5,693,792 | A | 12/1997 | Torii et al.     |
| 5,697,902 | A | 12/1997 | Goldenberg       |
| 5,703,057 | A | 12/1997 | Johnston et al.  |
| 5,714,350 | A | 2/1998  | Co et al.        |
| 5,721,367 | A | 2/1998  | Kay et al.       |
| 5,733,743 | A | 3/1998  | Johnson et al.   |
| 5,741,957 | A | 4/1998  | Deboer et al.    |
| 5,750,172 | A | 5/1998  | Meade et al.     |
| 5,756,687 | A | 5/1998  | Denman et al.    |
| 5,759,546 | A | 6/1998  | Weinberg et al.  |
| 5,770,197 | A | 6/1998  | Linsley et al.   |
| 5,770,429 | A | 6/1998  | Lonberg et al.   |
| 5,773,253 | A | 6/1998  | Linsley et al.   |
| 5,777,085 | A | 7/1998  | Co et al.        |
| 5,789,215 | A | 8/1998  | Berns et al.     |
| 5,789,650 | A | 8/1998  | Lonberg et al.   |
| 5,811,097 | A | 9/1998  | Allison et al.   |
| 5,814,318 | A | 9/1998  | Lonberg et al.   |
| 5,821,332 | A | 10/1998 | Godfrey et al.   |
| 5,827,690 | A | 10/1998 | Meade et al.     |
| 5,844,095 | A | 12/1998 | Linsley et al.   |
| 5,855,887 | A | 1/1999  | Allison et al.   |
| 5,874,299 | A | 2/1999  | Lonberg et al.   |
| 5,877,397 | A | 3/1999  | Lonberg et al.   |
| 5,885,796 | A | 3/1999  | Linsely et al.   |
| 5,916,771 | A | 6/1999  | Hori et al.      |
| 5,939,598 | A | 8/1999  | Kucherlapati et al.|
| 5,968,510 | A | 10/1999 | Linsley et al.   |
| 5,977,318 | A | 11/1999 | Linsley et al.   |
| 6,051,227 | A | 4/2000  | Allison et al.   |

(Continued)

FOREIGN PATENT DOCUMENTS

CA    2205680    11/1998

(Continued)

OTHER PUBLICATIONS

Chambers CA, et al., "CTLA-4-mediated inhibition in regulation of T cell responses: mechanisms and manipulation in tumor immunotherapy," *Annu Rev Immunol.* (2001);19:565-94.
U.S. Appl. No. 60/372,284, filed Apr. 12, 2002, Davis et al.
U.S. Appl. No. 60/293,042, filed May 23, 2001, Mueller et al.
Blair, et al., 1998, "Cutting Edge: CTLA-4 Ligation Delivers a Unique Signal to Resting Human CD4 T Cells That Inhibits Interleukin-2 Secretion but Allows Bcl-$X_L$ Induction," *J. of Immunology*, vol. 160: p. 12-15.
Bluestone, J., 1997, "Is CTLA-4 a Master Switch for Peripheral T Cell Tolerance?", *J. of Immunology*, vol. 158: p. 1989-1993.
Brunet, et al., 1988, "A Differential Molecular Biology Search for Genes Preferentially Expressed in Functional T Lymphocytes: The CTLA Genes," *Immunological Reviews*, vol. 103: p. 21-36.

(Continued)

*Primary Examiner* — Ilia Ouspenski
(74) *Attorney, Agent, or Firm* — Baker Botts L.L.P.

(57) ABSTRACT

The present invention provides method of treatment using human sequence antibodies against human CTLA-4 linked to a cytotoxic agent. In particular, methods of treating cancer and autoimmune disease are provided.

75 Claims, 4 Drawing Sheets

U.S. PATENT DOCUMENTS

| | | | |
|---|---|---|---|
| 6,075,181 | A | 6/2000 | Kucherlapati et al. |
| 6,114,598 | A | 9/2000 | Kucherlapati et al. |
| 6,150,584 | A | 11/2000 | Kucherlapati et al. |
| 6,162,963 | A | 12/2000 | Kucherlapati et al. |
| 6,207,156 | B1 | 3/2001 | Kuchroo et al. |
| 6,255,458 | B1 | 7/2001 | Lonberg et al. |
| 6,632,927 | B2 | 10/2003 | Adair et al. |
| 6,682,736 | B1 | 1/2004 | Hanson et al. |
| 6,719,972 | B1 | 4/2004 | Gribben et al. |
| 6,984,720 | B1 | 1/2006 | Korman et al. |
| 7,034,121 | B2 | 4/2006 | Carreno et al. |
| 7,229,628 | B1 | 6/2007 | Allison et al. |
| 7,410,253 | B2 | 8/2008 | Haberman et al. |
| 7,452,535 | B2 * | 11/2008 | Davis et al. ............. 424/130.1 |
| 7,465,446 | B2 | 12/2008 | Lowy et al. |
| 2001/0036458 | A1 | 11/2001 | Hiserodt et al. |
| 2002/0039581 | A1 | 4/2002 | Carreno et al. |
| 2002/0086014 | A1 | 7/2002 | Korman et al. |
| 2002/0182218 | A1 | 12/2002 | Nicolette |
| 2003/0086930 | A1 | 5/2003 | Mueller et al. |
| 2003/0175250 | A1 | 9/2003 | Jager et al. |
| 2005/0249700 | A1 | 11/2005 | Allison et al. |
| 2006/0034844 | A1 | 2/2006 | Allison et al. |
| 2007/0160619 | A1 | 7/2007 | Nichol et al. |
| 2007/0248595 | A1 | 10/2007 | Yang et al. |
| 2009/0074752 | A1 | 3/2009 | Lowy et al. |
| 2009/0117037 | A1 | 5/2009 | Davis et al. |
| 2009/0217401 | A1 * | 8/2009 | Korman et al. ............. 800/18 |
| 2010/0047244 | A1 * | 2/2010 | Korman et al. ........... 424/138.1 |

FOREIGN PATENT DOCUMENTS

| | | |
|---|---|---|
| EP | 0 216 846 | 4/1987 |
| EP | 0 256 055 | 2/1988 |
| EP | 0 323 997 | 7/1989 |
| EP | 0 338 841 | 10/1989 |
| EP | 0 463 151 | 1/1992 |
| EP | 0 546 073 | 6/1993 |
| EP | 0613944 | 9/1994 |
| EP | 0682039 | 11/1995 |
| EP | 1 262 193 A1 | 12/2002 |
| WO | WO 90/04036 | 4/1990 |
| WO | WO 91/10741 | 7/1991 |
| WO | WO 92/03918 | 3/1992 |
| WO | WO 92/22645 | 12/1992 |
| WO | WO 92/22647 | 12/1992 |
| WO | WO 92/22670 | 12/1992 |
| WO | WO 93/00431 | 1/1993 |
| WO | WO 93/12227 | 6/1993 |
| WO | WO 94/02602 | 2/1994 |
| WO | WO 94/25585 | 11/1994 |
| WO | WO 94/29444 | 12/1994 |
| WO | WO 95/01994 | 1/1995 |
| WO | WO 95/03408 | 2/1995 |
| WO | WO 95/05464 | 2/1995 |
| WO | WO 95/23859 | 9/1995 |
| WO | WO 95/24217 | 9/1995 |
| WO | WO 95/33770 | 12/1995 |
| WO | WO 95/34320 | 12/1995 |
| WO | WO 96/14436 | 5/1996 |
| WO | WO 96/14865 | 5/1996 |
| WO | WO 96/22380 | 7/1996 |
| WO | WO 96/33735 | 10/1996 |
| WO | WO 96/34096 | 10/1996 |
| WO | WO 97/07671 | 3/1997 |
| WO | WO 97/13852 | 4/1997 |
| WO | WO 97/20574 | 6/1997 |
| WO | WO 97/38137 | 10/1997 |
| WO | WO 98/24884 | 6/1998 |
| WO | WO 98/24893 A2 | 6/1998 |
| WO | WO 98/24893 A3 | 6/1998 |
| WO | WO 98/37757 | 9/1998 |
| WO | WO 98/42752 | 10/1998 |
| WO | WO 98/46996 | 10/1998 |
| WO | WO 98/50433 | 11/1998 |
| WO | WO 00/00569 | 1/2000 |
| WO | WO 00/10383 | 3/2000 |
| WO | WO 00/32231 | 6/2000 |
| WO | WO 00/37504 | 6/2000 |
| WO | WO 01/14424 | 3/2001 |
| WO | WO 03/086459 | 10/2003 |
| WO | WO 2005/003298 | 1/2005 |

OTHER PUBLICATIONS

Brunet, et al., 1987, "A new member of the immunoglubulin superfamily—CTLA-4," *Nature*, vol. 328: p. 267-270.

Chambers and Allison, 1997, "Co-stimulation in T cell responses," *Current Opinion in Immunology*, vol. 9:p. 396-404.

Chambers, et al., 1999, "Cytotoxic T lymphocyte antigen-4 (CTLA-4) regulates primary and secondary peptide-specific $CD3^+$ T cell responses," *Proc. Natl. Acad. Sci. USA*, vol. 96: p. 8603-8608.

Chambers et al., 1998, "Secondary but not primary T cell responses are enhanced in CTLA-4-deficient $CD8^+$ T cells," *Eur. J. Immunol.*, vol. 28: p. 3137-43.

Chambers, et al., 1997, "Lymphoproliferation in CTLA-4-Deficient Mice Is Mediated by Costimulation-Dependent Activation of CD4+ T Cells," *Immunity*, vol. 7: p. 885-895.

Chen, et al., "Immunoglobnulin gene rearrangement in B cell deficient mice generated by target deletion of the Jh locus," International Immunology, vol. 5, No. 6: p. 647-656.

Choi, et al., 1993, "Transgenic mice containing a human chain immunoglobulin gene fragment cloned in a yeast artificial chromosome," *Nature Genetics*, vol. 4.

Clark, et al., 1986, "Polypeptides on Human B Lymphocytes Associated with Cell Activation," *Human Immunology*, vol. 16: p. 100-113.

Damle, et al., 1981, "Monoclonal antibody analysis of human T lymphocyte subpopulations exhibiting autologous mixed lymphocyte reaction," *Proc. Natl. Acad. Sci. USA*, vol. 78: p. 5096-5098.

Dariavach, et al., 1988, "Human Ig superfamily CTLA-4 gene: chromosomal localization and identity of protein sequence between murine and human CTLA-4 cytoplasmic domains," *Eur. J. Immunol.*, vol. 18: p. 1901-1905.

Doyle, et al., 2001, "Induction of cytotoxic T lymphocyte antigen 4 (CTLA-4) restricts clonal expansion of helper T cells," *J. Exp. Med.*, vol. 194: p. 893-902.

Egen, et al., 2002, "CTLA-4: new insights into its biological function and use in tumor immunotherapy," *Nat. Immunol.*, vol. 3: p. 611-18.

Falko-Gunter Falkner,—F.3d—, 2006 WL 1453040, 1-15.

Fishwild, et al., 1996, "High-avidity human IgG kappa monoclonal antibodies from novel strain of minilocus transgenic mice," *Nature Biotechnology*, vol. 14: p. 845-851.

Freedman, et al., 1987, "B7, a B cell-restricted antigen that identifies preactivated B cells," *The J. of Immunology*, vol. 139: p. 3260-3267.

Freeman, et al., 1989, "B7, a new member of the Ig superfamily with unique expression on activated and neoplastic B cells," *The J. of Immunology*, vol. 143: p. 2714-2722.

Green, et al., 1998, "Regulation of B Cell Development by Variable Gene Complexity in Mice Reconstitution with Human Immunoglobulin Yeast Artificial Chromosome," *J. Exp. Med.*, vol. 188, No. 3: p. 483-495.

Green, et al., 1994, "Antigen-specific human monoclonal antibodies from mice engineered with human Ig heavy and light chain YAC's," *Nature Genetics*, vol. 7.

Gribben, et al., 1995, "CTLA4 mediates antigen-specific apoptosis of human T cells," *Proc. Natl. Acad. Sci. USA*, vol. 92: p. 811-815.

Hodi et al., 2003, "Biologic activity of cytotoxic T lymphocyte-associated antigen 4 antibody blockade in previously vaccinated metastatic melanoma and ovarian carcinoma patients," *Proc. Natl. Acad. Sci. USA*, vol. 100: p. 4712-17.

Hodi and Dranoff, 2006, "Combinatorial cancer immunotherapy," *Adv. Immunol.*, vol. 90: p. 341-68.

Hurwitz, et al., 1998, "CTLA-4 blockade synergizes with tumor-derived granulocyte-macrophage colony-stimulating factor for treatment of an experimental mammary carcinoma," *Proc. Natl. Acad. Sci. USA*, vol. 95: p. 10067-10071.

Hurwitz, et al., 2000, "Immunotherapy of Primary Prostate Cancer in a Transgenic Model Using a Combination of CTLA-4 Blockade and Tumor Cell Vaccine," *Cancer Research*, vol. 60: p. 2444-2448.

Jago et al., 2004, "Differential expression of CTLA-4 among T cell subsets," *Clin. Exp. Immunol.*, vol. 136: p. 463-71.

Kearney, et al., 1995, "Antigen-Dependent Clonal Expansion of a Trace Population of Antigen-Specific CD4+ T Cells In Vivo Is Dependent on CD28 Costimulation and Inhibited by CTLA-4," The J. of Immunology, vol. 155: 1032-1036.

Keler et al., 2003, "Activity and safety of CTLA-4 blockade combined with vaccines in Cynomolgus Macaques," J. Immunol., vol. 171: p. 6251-59.

Kohno, et al., 1990, "CD28 Molecule as a Receptor-like Function for Accessory Signals in Cell-Mediated Augmentation of IL-2 Production," Cellular Immunology, vol. 131; p. 1-10.

Krummel and Allison, 1995, "CD28 and CTLA-4 Have Opposing Effects on the Response of T cells to Stimulation," J. Exp. Med., vol. 182: p. 459-465.

Krummel and Allison, 1996, "CTLA-4 Engagement Inhibits IL-2 Accumulation and Cell Cycle Progression upon Activation of Resting T Cells," J. Exp. Med., vol. 138: p. 2533-2540.

Krummel, et al., 1995, "Superantigen responses and co-stimulation: CD28 and CTLA-4 have opposing effects on T cell expansion in vitro and in vivo," International Immunology, vol. 8: p. 519-523.

Kwon, et al., 1997, "Manipulation of T cell costimulatory and inhibitory signals for immunotherapy of prostate cancer," Proc. Natl. Acad. Sci. USA, vol. 94: p. 8099-8103.

Lafage-Pochitaloff, et al., 1990, "Human CD28 and CTLA-4 Ig superfamily genes are located on chromosome 2 at bands q33-q34," Immunogenetics, vol. 31: p. 198-201.

Leach, et al., 1996, "Enhancement of Antitumor Immunity by CTLA-4 Blockade," Science, vol. 271: p. 1734-1736.

Lesslauer, et al., 1986, "T90/44 (9.3 antigen). A cell surface molecule with a function in human T cell activation," Eur. J. Immunol., vol. 16: p. 1289-1296.

Lindsten, et al., 1989, "Regulation of Lymphokine Messenger RNA Stability by a Surface-Mediated T Cell Activation Pathway," Science, vol. 244: p. 339-343.

Linsley, et al., 1992, "Coexpression and Functional Cooperation of CTLA-4 and CD28 on Activated T Lymphocytes," J. Exp. Med., vol. 176: p. 1595-1604.

Linsley, et al., 1991, "CTLA-4 Is a Second Receptor for the B Cell Activation Antigen B7," J. Exp. Med., vol. 174: p. 561-569.

Linsley, et al., 1991, "Binding of the B Cell Activation Antigen B7 to CD28 Costimulates T Cell Proliferation and Interleukin 2 mRNA Accumulation," J. Exp. Med., vol. 173: p. 721-730.

Linsley, et al., 1990, "T-cell antigen CD28 mediates adhesion with B cells by interacting with activation antigen B7/BB-1," Proc. Natl. Acad. Sci. USA, vol. 87: 5031-5035.

Lonberg, et al., 1994, "Antigen-specific human antibodies from mice comprising four distinct genetic modifications," Nature, vol. 368.

Lonberg and Huszar, 1995, "Human Antibodies from Transgenic Mice," Intern. Rev. Immunol., vol. 13: p. 65-93.

Luhder, et al., 1998, "Cytotoxic T Lymphocyte-associated Antigen 4 (CTLA-4) Regulates the Unfolding of Autoimmune Diabetes," J. Exp. Med., vol. 187: p. 427-432.

Macon-Lemaitre and Triebel, 2005, "The negative regulatory function of the lymphocyte-activation gene-3 co-receptor (CD223) on human T cells," Immunology, vol. 115: p. 10-178.

Matsui, et al., 1999, "Autoantibodies to T Cell Costimulatory Molecules in Systemic Autoimmune Diseases," The J. of Immunology, vol. 162: p. 4328-4335.

McCoy, et al., 1997, "Protective Immunity to Nematode Infection Is Induced by CTLA-4 Blockade," J. Exp. Med., vol. 186: p. 183-187.

Mendez, et al., 1997, "Functional transplant of megabase human immunoglobulin loci recapitulates human antibody response in mice," Nature Genetics, vol. 15.

Metz, et al., 1998, "Differential role of CTLA-4 in regulation of resting memory versus naive CD4 T cell activation," J. Immunol., vol. 161: p. 5855-61.

Mokyr, et al., 1998, "Realization of the therapeutic potential of CTLA—4 blockade in low-dose chemotherapy-treated tumor-bearing mice," Cancer Research, American Association for Cancer Research, vol. 58, No. 23: p. 5301-5304.

Neuberger, M., 1996, "Generating high-avidity human Mabs in mice," Nature Biotechnology, vol. 14: p. 826.

Ribas et al., 2005, "Role of dendritic cell phenotype, determinant spreading, and negative costimulatory blockade in dendritic cell-based melanoma immunotherapy," J. Immunother., vol. 27: p. 354-67.

Rosenberg, "A new era for cancer immunotherapy based on the genes that encode cancer antigens," Immunity, 1999; 10:281-7.

Taylor, et al., 1992, "A transgenic mouse that expresses a diversity of human sequence heavy and light chain immunoglobulins," Nucleic Acids research, vol. 20, No. 23: p. 6287-6295.

Taylor, et al., "Human Immunoglobulin transgenes undergo rearrangement, somatic mutation and class switching in mice that lack endogenous IgM," International Immunology, vol. 6, No. 4: p. 579-591.

Thompson and Allison, 1997, "The Emerging Role of CTLA-4 as an Immune Attenuator," Immunity, vol. 7: p. 445-450.

Thompson, et al., 1989, "CD28 activation pathway regulates the production of multiple T-cell-derived lymphokines/cytokines," Proc. Natl. Acad. Sci. USA, vol. 86: p. 1333-1337.

Tivol, et al., 1995, Immunity, vol. 3: p. 541-547.

Tuaillon, et al., 1993, "Human immunoglobulin heavy-chain minilocus recombination in transgenic mice: Gene-segment use in u and y transcripts," Proc. Natl. Acad. Sci. USA., vol. 99: p. 3720-3724.

Tuaillon, et al., 1995, "Analysis of Direct and Inverted DJh Rearrangements in a Human Ig Heavy Chain Transgenic Minilocus," The Journal of Immunology, vol. 154: p. 6453-6465.

van Elsas, et al., 1999, "Combination Immunotherapy of B16 Melanoma Using Anti-Cytotoxic T Lymphocyte-associate Antigen 4 (CTLA-4) and Granulocyte/Macrophage Colony-Stimulating Factor (GM-CSF)-producing Vaccines Induces Rejection of Subcutaneous and Metastatic Tumors Accompanied by Autoimmune Depigmentation," J. Exp. Med., vol. 190: p. 355-366.

van Elsas, et al., 2001 "Elucidating the Autoimmune and Antitumor Effector Mechanisms of a Treatment Based on Cytomtoxic T Lymphocyte Antigen-4 Blockade in Combination with B16 Melanoma Vaccine: Comparison of Prophylaxis and Therapy," J. Exp. Med., vol. 194, No. 4: p. 481-489.

Walunas, et al., 1996, "CTLA-4 Ligation Blocks CD28-dependent T Cell Activation," J. Exp. Med., vol. 183: p. 2541-2550.

Walunas, et al., 1994, "CTLA-4 Can Function as a Negative Regulator of T Cell Activation," Immunity, vol. 1: p. 405-413.

Wu, et al., 1997, "CTLA-4 B7 Interaction Is Sufficient to Costimulate T Cell Clonal Expansion," J. Exp. Med., vol. 185: p. 1327-1335.

Yang, et al., 1999, "Eradication of Established Tumors by Fully Human Monoclonal Antibody to the Epidermal Growth Factor Receptor without Concomitant Chemotherapy," Cancer Research, vol. 59: p. 1236-1243.

Yokochi, et al., 1982, "B lymphoblast antigen (BB-1) expressed on Epstein-Barr virus-activated B cell blasts, B lymphoblastoid cell lines, and Burkitt's lymphomas," The J. of Immunology, vol. 128: p. 823-827.

Zenapax® package insert and information, 2005.

U.S. Appl. No. 09/705,346, filed Nov. 2, 2000, Allison et al.

U.S. Appl. No. 10/319,832, filed Dec. 12, 2002, Allison et al.

U.S. Appl. No. 10/411,973 (issued as US 7,452,535 on Nov. 18, 2008), filed Apr. 11, 2003.

U.S. Appl. No. 09/644,668 (issued as US 6,984,720 on Jan. 10, 2006), filed Aug. 24, 2000.

U.S. Appl. No. 09/948,939 (issued as US 7,605,238 on Oct. 20, 2009), filed Sep. 7, 2001.

U.S. Appl. No. 10/409,705 (Abandoned), filed Apr. 4, 2003.

U.S. Appl. No. 11/040,846 (Abandoned), filed Jan. 20, 2005.

U.S. Appl. No. 12/564,756 (issued as US 8,017,114 on Sep. 13, 2011), filed Sep. 22, 2009.

U.S. Appl. No. 13/198,263, filed Aug. 4, 2011.

U.S. Appl. No. 10/857,749 (issued as US 7,465,446 on Dec. 16, 2008), filed May 27, 2004.

U.S. Appl. No. 11/557,835 (issued as US 7,611,702 on Nov. 3, 2009), filed Nov. 8, 2006.

U.S. Appl. No. 11/567,846 (published as US 20070160619A1 on Jul. 12, 2007), filed Dec. 7, 2006.

U.S. Appl. No. 12/259,075 (issued as US 7,744,875 on Jun. 29, 2010), filed Oct. 27, 2008.

Anderson, DE, et al., "Paradoxical inhibition of T-cell function in response to CTLA-4 blockade; heterogeneity within the human T-cell population," Nature Medicine (2000), vol. 6: 211-214.

Ansell et al., "Phase I study of ipilimumab, an anti-CTLA-4 monoclonal antibody, in patients with relapsed and refractory B-cell non-hodgkin lymphoma," *Clin. Cancer Res.* (2009);15(20):6446-6453.

Attia, et al. "Autoimmunity correlates with tumor regression in patients with metastatic melanoma treated with anti-cytotoxic T-lymphocyte antigen-4." J Clin Oncol. Sep. 1, 2005; vol. 23(25):6043-53.

Balint et al., "Antibody engineering by parsimonious mutagenesis", Gene, 137 (1993): 109-118.

Balzano, et al."CTLA-4 and CD28: similar proteins, neighbouring genes." Int J Cancer Suppl. 1992;7:28-32.Links.

Barbas et al., "Recognition of DNA by Synthetic Antibodies," *J. Am. Chem. Soc.* (1994) 116: 2161-2162.

Barbas et al., "Human autoantibody recognition of DNA," *Proc. Natl. Acad. Sci. USA* (1995) 92: 2529-2533.

Bashey et al., "CTLA-4 blockade with ipilimumab to treat relapse of malignancy after allogeneic hematopoietic cell transplantation," *Blood* (2009);113:1581-1588.

Bashey et al., "Phase I study of a neutralizing monoclonal anti-CTLA-4 antibody (MDX-010) in patients with relapse of malignancy after allogeneic hematopoietic stem cell transplantation," *Biology of Blood and Marrow Transplantation* (2005);11(2):5.

Beck et al., "Enterocolitis in patients with cancer after antibody blockade of cytotoxic T-lymphocyte-associated antigen 4," *J Clin Oncol.* (2006);24(15):2283-9.

Beckman et al., "Antibody constructs in cancer therapy", Can. 109: 170-179 (2007).

Beiboer et al., "Guided Selection of a Pan Carcinoma Specific Antibody Reveals Similar Binding Characteristics yet Structural Divergence Between the Original Murine Antibody and its Human Equivalent," *J. Mol. Biol.* (2000) 296: 833-849.

Bi et al., "Expressions of Fas, CTLA-4 and RhoBTB2 genes in breast carcinoma ad their relationship with clinicopathological factors", Zhonghua Zhong Liu Za Zhi. Oct. 2008; 30(10): 749-53 (Articles is in Chinese, English Abstract submitted).

Bluestone J.A., "New perspective of CD28-B7-Mediated minireview T cell costimulation", Immunity 2: 555-559 (1995).

Boon, T. et al., "Toward a genetic analysis of tumor rejection antigens", (1992) Advances in Cancer Res. 58: 177-210.

Brown et al., "Tumor necrosis factor antagonist therapy and lymphoma development", (2002) *Arthritis and Rheumatism*, 46(12): 3151-3158.

Camacho et al., "Phase I/II Trial of Tremelimumab in patients with metastatic melanoma," *J. Clin. Oncol.* (2009);27:1075-1081.

Camacho et al., "Phase 1 clinical trial of anti-CTLA4 human monoclonal antibody CP-675,206 in patients (pts) with advanced solid malignancies," *J. Clin. Oncol.* 2004 ASCO Annual Meeting Proceedings (Post-Meeting Edition), vol. 22, No. 14S (Jul. 15 Suppl.), 2004:2505.

Cancer Therapy Evaluation Program, Common Terminology Criteria for Adverse Events (CTCAE), Version 3.0, DCTD, NCI, NIH, DHHS, Mar. 31, 2003.

Cespedes et al., "Mouse models in oncogenesis and cancer therapy", Clin. Transl. Oncol. 8(5): 318-329 (2006).

Chambers, CA, et al., "Thymocyte development is normal in CTLA-4-deficient mice," Proceedings of the National Academy of Sciences USA (1997), vol. 94: 9296-9301.

Chang and Siegel "Genetic and immunological properties of phage-displayed human anti-Rh(D) antibodies: implications for Rh(D) epitope topology," *Am. Soc. Hematol* (1998) 21(8): 3066-3078.

Chen et al., "Costimulation of Antitumor Immunity by the B7 Counterreceptor for the T Lymphocyte Molecules CD28 and CTLA-4," Cell 71:1093-1102 (1992).

Damle et al., "Alloantigen-specific cytotoxic and suppressor T lymphocytes are derived from phenotypically distinct precursors," *J Immunol.* (1983);131(5):2296-300.

Damle et al., "Costimulation of T Lymphocytes with Integrin Ligands Intercellular Adhesion Molecule-1 or Vascular Cell Adhesion Molecule-1 Induces Functional Expression of CTLA-4, A Second Receptor for B7," Journal of Immunology 152:2686-2697 (1994).

Dennis, C., "Cancer: off by a whisker", *Nature* 442: 739-741 (2006).

Ditzel et al., "Determinants of Polyreactivity in a Large Panel of Recombinant Human Antibodies from HIV-1 Infection," *The Journal of Immunology* (1996) 157:739-749.

Downey et al., "Prognostic factors related to clinical response in patients with metastatic melanoma treated by CTL-associated antigen-4 blockade", *Clin. Cancer Res.* 13(22): 6681-6688 (Nov. 2007).

European Search Report for EP 03728392.6, dated Apr. 29, 2005.

Frankel, Arthur E., "Increased sophistication of immunotoxins" Clinical Cancer Research, vol. 8: 942-944 (Apr. 2002).

Freeman, G.J. et al., "CTLA-4 and CD28 mRNA are coexpressed in most T cells after Activation", J. Immunol. 149(12): 3795-3801 (1992).

Freeman et al., "Uncovering of Functional Alternative CTLA-4 Counter-Receptor in B7-Deficient Mice," Science 262: 907-909 (1993).

Fujimori et al., J. Nuc. Med. 31:1191-1198, (1990).

Gray et al., "Therapeutic potential of immunostimulatory monoclonal antibodies", *Clinical Science*, 2006, 111:93-106.

Gribben, G, et al., "Alloantigen and concomitant CTLA4 signaling induces clonal deletion of alloreactive T cells", Blood (1994), vol. 84: 397a (meeting abstract).

Gulley et al., "Future directions in tumor immunotherapy", *Nat Clin Pract Oncol.* (2007); 4(3): 136-137.

Gura et al., "Systems for identifying new drugs are often faulty", *Science* 278: 1041-1042 (Nov. 1997).

Harding et al., "CD28-Mediated Signaling Co-Stimulates Murine T Cells and Prevents Induction of Energy in T-Cell Clones," Nature 356: 607-609 (1992).

Heslop, HE, "Cytokine gene transfer in the therapy of malignancy," Baillieres Clinical Hematology (1994), vol. 7, pp. 135-151 (abstract only), Medline 8038497.

Hochberg et al., "The benefit/risk profile of TNF-Blocking agents: Findings of a consensus panel", *Semin. Arthritis Rheum.*, 2005, 34:819-836.

Hodi et al., "Immunologic and clinical effects of antibody blockade of cytotoxic T lymphocyte-associated antigen 4 in previously vaccinated cancer patients," *PNAS* (2008);105(8):3005-3010.

Honjo and Matsuda, "Immunoglobulin heavy chain loci of mouse and human," *Immunoglobulin Genes*, Second Ed., (1995) edited by To Hanjo and F.W. Alt, Academic Press, Chapter 7.

Huang, Z., "Structural chemistry and therapeutic intervention of protein-portein interactions in immune response, human immunodeficiency virus entry, and apoptosis", *Pharmacology and Therapeutics*, 2000, 86: 201-215.

Hurwitz et al., "Combination immunotherapy of primary prostate cancer in a transgenic mouse model using CTLA-4 blockade," *Cancer Res.* (2000);60(9):2444-8.

International Search Report for PCT/US2004/016995, mailed May 10, 2005.

Ishida et al., "Production of a diverse repertoire of human antibodies in genetically engineered mice," *Microbiol. Immunol.* (1998) 42(3):143-50.

Jaberipour M, et al., "Increased CTLA-4 and FOXP3 Transcripts in Peripheral Blood Mononuclear Cells of Patients with Breast Cancer," Pathol Oncol Res. Mar. 21, 2010. [Epub ahead of print].

Jain, R.K., "Barriers to drug delivery in solid tumors", Scientific American, Jul. 1994, pp. 58-65.

Janik et al., "A pilot study of MDX-010 after vaccine failure in patients with advanced malignancy," Blood (2003);102(11):647A, Abstract No. 2391.

Jenkins, M.K., "The Ups and Downs of T Cell Costimulation," Immunity 1: 443-446 (1994).

June et al., "The B7 and CD28 Receptor Families," Immunology Today, 15(7): 321-331 (1994).

Klimka et al., "Human anti-CD30 recombinant antibodies by guided phage antibody selection using cell panning," *British Journal of Cancer* (2000) 83(2): 252-260.

Langer et al., "Updated on anti-CTLA-4 antibodies in clinical trials", *Expert. Opin. Biol. Ther.* 7(8): 1245-1256 (2007).

Lee, K-H, et al., "Increased vaccine-specific T cell frequency after peptide-based vaccination correlates with increased susceptibility to in vitro stimulation but does not lead to tumor regression," Journal of Immunology (1999), vol. 163: 6292-6300.

Lenschow et al., "Long-Term Survival of Xenogeneic Pancreatic Islet Grafts Induced by CTLA4Ig," Science 257: 789-792 (1992).

Lenschow et al., "Expression and Functional Significance of an Additional Ligand for CTLA-4," Proc. Natl. Acad. Sci. USA 90: 11054-11058 (1993).

Lin et al., "Long-Term Acceptance of Major Histocompatibility Complex Mismatched Cardiac Allografts Induced by CTLA4Ig Plus Donor-Specific Transfusion," J. Exp. Med. 178: 1801-1806 (1993).

Lindsten et al., "Characterization of CTLA-4 structure and expression on human T cells" The Journal of Immunology, 151(7): 3489-3499 (Oct. 1, 1993).

Linsley, P.S., "Distinct roles for CD28 and cytotoxic T lymphocyte-associated molecule-4 receptors during T cell activation?" J. Exp. Med., The Rockefeller University Press, vol. 182, Aug. 1995: 289-292.

Linsley et al., "Immunosuppression in Vivo by a Soluble Form of the CTLA-4 T Cell Activation Molecule," Science 257: 792-795 (1992).

Linsley, P.S., et al., "CD28 engagement by B7/BB-1 induces transient down-regulation of CD28 synthesis and prolonged unresponsiveness to CD28 signaling", J. Immunol. 150: 3161-3169 (1993).

Linsley, P.S. and J.A. Ledbetter, "The Role of the CD28 Receptor During T Cell Responses to Antigen," Ann. Rev. Immunol. 11:191-212 (1993).

Maker et al., "Intrapatient dose escalation of anti-CTLA-4 antibody in patients with metastatic melanoma", J. Immunother. 29(4): 455-463 (2006).

Mukherji, B. et al., "Induction of antigen-specific cytolytic T cells in situ in human melanoma by immunization with synthetic peptide-pulsed autologous antigen presenting cells", (1995) Proc. Natl. Acad. Sci. USA. 92: 8078-8092.

Murata, et al. "Expression of the costimulatory molecule BB-1, the ligands CTLA-4 and CD28, and their mRNA in inflammatory myopathies." Am J Pathol. Aug. 1999; vol. 155 (2):453-60.

O'Mahony et al., "A pilot study of CTLA-4 blockade after cancer vaccine failure in patients with advanced malignancy," Clin Cancer Res. (2007);13(3):958-964.

Overwijk et al., "Vaccination with a recombinant vaccinia virus encoding a "self" antigen induces autoimmune vitiligo and tumor cell destruction in mice: requirement for CD4(+) T lymphocytes," Proc Natl Acad Sci U S A. (1999);96(6):2982-7.

Panka et al., "Variable region framework differences result in decreased or increased affinity of variant anti-digoxin antibodies", (1988) Porc. Natl. Acad. Sci. USA, 85:3080-3084.

Perrin et al., "CTLA-4 blockade enhances clinical disease and cytokine production during experimental allergic encephalomyelitis," J Immunol. (1996);157(4):1333-6.

Phan et al., "Cancer regression and autoimmunity induced by cytotoxic T lymphocyte-associated antigen 4 blockade in patients with metastatic melanoma," Proc Natl Acad Sci U S A. (2003);100(14):8372-7.

Rader et al., "A phage display approach for rapid antibody humanization: Designed combinatorial V gene libraries," Proc. Natl. Acad. Sci. USA (1998) 95: 8910-8915.

Rosenberg and White, "Vitiligo in patients with melanoma: normal tissue antigens can be targets for cancer immunotherapy," J Immunother Emphasis Tumor Immunol. (1996);19(1):81-4.

Rudikoff et al., "Single amino acid substitution altering antigen-binding specificity", (1982) Proc. Natl. Acad. Sci. USA, 79: 1979-1983.

Rudnick et al., "Affinity and avidity in antibody-based tumor targeting", Can. Biotherp. & Radiopharm. 24: 155-162 (2009).

Saenger et al., Can. Immun. 8: 1-7 (Jan. 2008).

Sanderson et al., "Autoimmunity in a phase I trial of a fully human anti-cytotoxic T-lymphocyte antigen-4 monoclonal antibody with multiple melanoma peptides and Montanide ISA 51 for patients with resected stages III and IV melanoma," J Clin Oncol. (2005);23(4):741-50.

Schäble and Zachau "The variable genes of the human immunoglobulin κ locus" Biol. Chem. (1993) 374(11): 1001-1022.

Schwartz, R.H., "Costimulation of T Lymphocytes: The Role of CD28, CTLA-4, and B7/BB1 in Interleukin-2 Production and Immunotherapy," Cell 71:1065-1068 (1992).

Shah KV, et al., "CTLA-4 is a direct target of Wnt/beta-catenin signaling and is expressed in human melanoma tumors," J Invest Dermatol. Dec. 2008;128(12):2870-9. Epub Jun. 19, 2008.

Shaw et al., "Adjuvant immunotherapy for patients with melanoma: are patients with melanoma of the head and neck candidates for this therapy?" Head and Neck (1997) 19: 595-603.

Small et al., "A pilot trial of CTLA-4 blockade with human anti-CTLA-4 in patients with hormone-refractory prostate cancer," Clin. Cancer Res. (2007);13(6):1810-1815.

Sotomayor, EM, et al., "In vivo blockade of CTLA-4 enhances the priming of responsive T cells but fails to prevent the induction of tumor antigen-specific tolerance," Proceedings of the National Academy of Science USA (1999), vol. 96: 11476-11481.

Spencer et al., "Distinct inflammatory mechanisms mediate early versus late colitis in mice", Gastroenterology, 2002, 122:94-105.

Sullivan, T.J. et al., "Induction of CNS inflammatory disease as a consequence of CTLA-4/B7 blockade," FASEB Journal (1998), vol. 12, pp. A1092; Abstract No. 6319 (meeting abstract).

Tarhini & Kirkwood, "Tremelimumab (CP-675,206) a fully human anticytotoxic T lymphocyte-associated antigen 4 monoclonal antibody for treatment of patients with advanced cancers," Expert Opin. Boil. Ther. (2008);8(10):1583-1593.

Tassev & Cheung, "Monoclonal antibody therapies for solid tumors," Expert. Opin. Biol. Ther. (2009);9(3):341-353.

Thompson et al., "CD28 activation pathway regulates the production of multiple T-cell-derived lymphokines/cytokines," Proc Natl Acad Sci U S A. (1989);86(4):1333-7.

Thurber et al., "Antibody tumor penetration: transport opposed by systemic and antigen-mediated clearance", Adv. Drug Deliv. Rev. 60: 1421-1434 (2008).

Timmerman, J.M. et al., "Dendritic cell vaccines for cancer immunotherapy," Annual Review of Medicine (1999), vol. 50: 507-529.

Titelbaum et al., "anti-tumor necrosis factor alpha-associated multiple sclerosis", AJNR Am J Neuroradiol, 26: 1548-1550, Jun./Jul. 2005.

Townsend, S.E. and J.P. Allison, "Tumor Rejection After Direct Costimulation of CD8+ T Cells by B7-Transfected Melanoma Cells," Science 259: 368-370 (1993).

Turka et al., "T-Cell Activation by the CD28 Ligand B7 is Required for Cardiac Allograft Rejection in vivo," Proc. Natl. Acad. Sci. USA 89: 11102-11105 (1992).

Underhill et al., "Phase I dose escalation trial of tremelimumab (CP-675,206) administered in combination with PF-3512676 in patients with melanoma or other advanced cancers," J. Clin. Oncol. (2009);27:15s (Suppl; abstract 3046).

Van Assche et al., Curr. Opin. Gastroenterol., Jul. 2005, 21: 443-447.

Voskoglou-Nomikos et al., "Clinical predictive value of the in vitro cell line, human xenograft, and mouse allograft preclinical cancer models", Clin. Can. res. 9: 4227-4239 (2003).

Weber JS. "Tumor evasion may occur via expression of regulatory molecules: a case for CTLA-4 in melanoma," J Invest Dermatol. Dec. 2008;128(12):2750-2.

Weber, J., "Review: Anti-CTLA-4 Antibody Ipilimumab: Case studies of clinical response and immune-related adverse events", The Oncologist, 12: 864-872 (2007).

Wen Y.J. et al., "Idiotypic protein-pulsed adherent peripheral blood mononuclear cell-derived dendritic cells prime immune system on multiple myeloma", (1998) Clin. Cancer Res. 4: 957-962.

Yang, Y-F, et al., "Enhanced induction of antitumor T-cell responses by cytotoxic lymphocyte-associated molecule-4 blockade: the effect is manifested only at the restricted tumor-bearing stages," Cancer Research (1997), vol. 57: 4036-4041.

Yang et al., "Ipilimumab (anti-CTLA4 antibody) causes regression of metastatic renal cell cancer associated with enteritis and hypophysitis," J. Immunother. (2007);30(8):825-830.

Yanofsky, S.D. et al., "High affinity type I interleukin receptor antagonists discovered by screening recombinant peptide libraries," (1996) Proc. Natl. Acad. Sci. USA 93: 7381-7386.

Zachau, "The human immunoglobulin K genes," *Immunoglobulin Genes*, Second Ed., (1995) edited by To Hanjo and F.W. Alt, Academic Press, Chapter 8.

Zaks, T.Z. and Rosenberg S.A., "Immunization with a peptide epitope (p369-377) from HER-2/neu leads to peptide-specific cytotoxic T lymphocytes that fail to recognize HER-2/neu+ tumors," Cancer Research (1998), vol. 58: 4902-4908.

Zhu, J. et al., "Cytotoxic T lymphocyte-associated antigen 4 (CTLA-4) blockade enhances incidence and severity of experimental autoimmune neuritis in resistant mice," Journal of Neuroimmunology (2001), 115: 111-117.

* cited by examiner

METHODS OF TREATMENT USING CTLA-4 ANTIBODIES

The application is a continuation of U.S. patent application Ser. No. 10/411,973 filed on Apr. 11, 2003, issued as U.S. Pat. No. 7,452,535, which claims priority to U.S. provisional patent application Ser. No. 60/372,284 filed on Apr. 12, 2002, and to U.S. provisional patent application Ser. No. 60/381,274 filed May 17, 2002, the disclosures of which are hereby incorporated by reference in their entirety.

SEQUENCE LISTING

The specification further incorporates by reference the Sequence Listing submitted herewith via EFS on May 2, 2011. Pursuant to 37 C.F.R. §1.52(e)(5), the Sequence Listing text file, identified as "0773750741SEQLIST.TXT," is 4,088 bytes and was created on May 2, 2011. The Sequence Listing, electronically filed herewith, does not extend beyond the scope of the specification and thus does not contain new matter.

FIELD OF THE INVENTION

The present invention relates generally to molecular immunology and the treatment of human diseases. In particular, it relates to novel treatment methods using antibodies against human CTLA-4.

BACKGROUND OF THE INVENTION

The vertebrate immune system requires multiple signals to achieve optimal immune activation (see, e.g., Janeway, Cold Spring Harbor Symp. Quant. Biol. 1989; 54:1-14; Paul William E., ed. Raven Press, N.Y., Fundamental Immunology, 4th edition (1998), particularly chapters 12 and 13, pages 411 to 478). Interactions between T lymphocytes (T cells) and antigen presenting cells (APC) are essential to the immune response. Levels of many cohesive molecules found on T cells and APC's increase during an immune response (Springer et al., A. Rev. Immunol. 1987; 5:223-252; Shaw and Shimuzu, Current Opinion in Immunology, 1988 Eds. Kindt and Long, 1:92-97; and Hemler, Immunology Today 1988; 9:109-113). Increased levels of these molecules may help explain why activated APC's are more effective at stimulating antigen-specific T cell proliferation than are resting APC's (Kaiuchi et al., J. Immunol. 1983; 131:109-114; Kreiger et al., J. Immunol. 1985; 135:2937-2945; McKenzie, J Immunol. 1988; 141:2907-2911; and Hawrylowicz and Unanue, J. Immunol. 1988; 141:4083-4088).

T cell immune response is a complex process that involves cell-cell interactions (Springer et al., A. Rev. Immunol. 1987; 5:223-252), particularly between T and accessory cells such as APCs, and production of soluble immune mediators (cytokines or lymphokines) (Dinarello, New Engl. J. Med 1987; 317:940-945; Sallusto, J. Exp. Med. 1997; 179:1109-1118). This response is regulated by several T-cell surface receptors, including the T-cell receptor complex (Weiss, Ann. Rev. Immunol. 1986; 4:593-619) and other "accessory" surface molecules (Allison, Curr. Opin. Immunol. 1994; 6:414-419; Springer, 1987, supra). Many of these accessory molecules are naturally occurring cell surface differentiation (CD) antigens defined by the reactivity of monoclonal antibodies on the surface of cells (McMichael, Ed., *Leukocyte Typing III*, Oxford Univ. Press, Oxford, N.Y., 1987).

T helper cell (Th) antigenic response requires signals provided by APC's. The first signal is initiated by interaction of the T cell receptor complex (Weiss, J. Clin. Invest. 1990, 86:1015) with antigen presented in the context of class II major histocompatibility complex (MHC) molecules on the APC (Allen, Immunol. Today 1987; 8:270). This antigen-specific signal is not sufficient to generate a full response, and in the absence of a second signal may actually lead to clonal inactivation or anergy (Schwartz, Science 1990; 248:1349). The requirement for a second "costimulatory" signal provided by the MHC has been demonstrated in a number of experimental systems (Schwartz, supra; Weaver and Unanue, Immunol. Today 1990; 11:49). The molecular nature of this second signal is not completely understood, although it is clear in some cases that both soluble molecules such as interleukin (IL)-1 (Weaver and Unanue, supra) and membrane receptors involved in intercellular adhesion (Springer, Nature 1990; 346:425) can provide costimulatory signals.

CD28 antigen, a homodimeric glycoprotein of the immunoglobulin superfamily (Aruffo and Seed, Proc. Natl. Acad. Sci. 1987; 84:8573-8577), is an accessory molecule found on most mature human T cells (Damle et al., J. Immunol. 1983; 131:2296-2300). Current evidence suggests that this molecule functions in an alternative T cell activation pathway distinct from that initiated by the T-cell receptor complex (June et al., Mol. Cell. Biol. 1987; 7:4472-4481). Monoclonal antibodies (MAbs) reactive with CD28 antigen can augment T cell responses initiated by various polyclonal stimuli (reviewed by June et al., supra). These stimulatory effects may result from MAb-induced cytokine production (Thompson et al., Proc. Natl. Acad. Sci 1989; 86:1333-1337; and Lindsten et al., Science 1989; 244:339-343) as a consequence of increased mRNA stabilization (Lindsten et al., 1989, supra). Anti-CD28 mAbs can also have inhibitory effects, i.e., they can block autologous mixed lymphocyte reactions (Damle et al., Proc. Natl. Acad. Sci. 1981; 78:5096-6001) and activation of antigen-specific T cell clones (Lesslauer et al., Eur. J. Immunol. 1986; 16:1289-1296).

CTLA-4 is a T cell surface molecule that was originally identified by differential screening of a murine cytolytic T cell cDNA library (Brunet et al., Nature 328:267-270 (1987)). CTLA-4 is also a member of the immunoglobulin (Ig) superfamily; CTLA-4 comprises a single extracellular Ig domain. CTLA-4 transcripts have been found in T cell populations having cytotoxic activity, suggesting that CTLA-4 might function in the cytolytic response (Brunet et al., supra; Brunet et al., Immunol. Rev. 103-21-36 (1988)). Researchers have reported the cloning and mapping of a gene for the human counterpart of CTLA-4 (Dariavach et al., *Eur. J Immunol.* 18:1901-1905 (1988)) to the same chromosomal region (2q33-34) as CD28 (Lafage-Pochitaloff et al., *Immunogenetics* 31: 198-201 (1990)). Sequence comparison between this human CTLA-4 DNA and that encoding CD28 proteins reveals significant homology of sequence, with the greatest degree of homology in the juxtamembrane and cytoplasmic regions (Brunet et al., 1988, supra; Dariavach et al., 1988, supra).

CTLA-4 is accepted as opposing CD28 activity and dampening T cell activation (Krummel, J. Exp. Med. 1995; 182:459-465; Krummel et al., Int'l Immunol. 1996; 8:519-523; Chambers et al., Immunity. 1997; 7:885-895). CTLA-4 deficient mice suffer from massive lymphoproliferation (Chambers et al., supra). It has been reported that CTLA-4 blockade augments T cell responses in vitro (Walunas et al., Immunity. 1994; 1:405-413) and in vivo (Kearney, J. Immunol. 1995; 155:1032-1 036), exacerbates antitumor immunity (Leach, Science 1996; 271: 1734-1736), and enhances an induced autoimmune disease (Luhder, J Exp. Med. 1998; 187:427-432). It has also been reported that CTLA-4 has an alternative or additional impact on the initial character of the T cell immune response (Chambers, Curr. Opin. Immunol. 1997; 9:396-404; Bluestone, J. Immunol. 1997; 158:1989-1993; Thompson, Immunity 1997; 7:445-450). This is consistent with the observation that some autoimmune patients have autoantibodies to CTLA-4. It is possible that CTLA-4 blocking autoantibodies playa pathogenic role in these patients (Matsui, J. Immunol. 1999; 162:4328-4335).

Non-human CTLA-4 antibodies have been used in the various studies discussed above. Furthermore, human antibodies against human CTLA-4 have been described as immunostimulation modulators in a number of disease conditions, such as treating or preventing viral and bacterial infection and for treating cancer (e.g., PCT Publication WO 01/14424 and PCT Publication WO 00/37504). U.S. Pat. No. 5,855,887 discloses a method of increasing the response of a mammalian T cell to antigenic stimulation by combining a T cell with a CTLA-4 blocking agent. U.S. Pat. No. 5,811,097 discloses a method of decreasing the growth of non-T cell tumors by administering a CTLA-4 blocking agent. U.S. patent application Ser. Nos. 09/644,668 and 09/948,939 disclose human CTLA-4 antibodies and are hereby incorporated by reference.

The citation or discussion of any reference in this section or elsewhere in the specification is made only to clarify the description of the present invention and is not an admission that any such reference is "prior art" against any invention described herein.

SUMMARY OF THE INVENTION

The present invention provides methods of promoting or potentiating a secondary or memory immune response using anti-CTLA4 antibodies. Anti-CTLA-4 antibodies demonstrate an ability to increase the magnitude of protective immunity in a subject already immunized to protective antigens from a pathogen, e.g., cancer antigens or antigens from an infectious agent. Such prior immunization may have occurred as a result of natural exposure, e.g., to cancer cells of a resected tumor or from resolved or suppressed infection with an infectious agent. Such patients can be tested for evidence of such exposure, i.e., for immunity to a protective antigen to the pathogen. Alternatively, the patient may have been vaccinated against the pathogen, in which case immunity can be presumed or tested.

In one embodiment, the CTLA4 antibodies of the invention can be used in the treatment of malignancies, where the patient has previously received a cancer vaccine or demonstrates some level of natural protective immunity to the tumor. The antibodies can be used as a single agent or in combination with one or more other agents, such as chemotherapy, radiation therapy, cytokines, chemokines and other biologic signaling molecules, tumor specific vaccines, autologous and allogeneic stem cell rescue (e.g., to augment graft versus tumor effects), other therapeutic antibodies, molecular targeted therapies, anti-angiogenic therapy, infectious agents with therapeutic intent (such as tumor localizing bacteria) and gene therapy. The antibodies can be administered as a single dose or as multiple doses. The antibodies can be used in adjuvant or neoadjuvant therapy, either alone or in conjunction with the aforementioned therapies.

Treatment with an anti-CTLA4 antibody can be used to activate a pre-existing memory response in patients treated with a cancer vaccine. Thus, vaccine-treated patients can be selected for further treatment with an anti-CTLA4 antibody to thereby further induce or enhance an immune response.

In one embodiment, the antigen is a cancer antigen and the patient has been previously treated with an anti-cancer vaccine. The cancer antigen can be, for example, melanoma antigen or a prostate cancer antigen. In another embodiment, the antigen is a viral antigen and the patient has been previously treated with a viral vaccine. The viral antigen can be, for example, a hepatitis antigen. In one embodiment, the patient is a human. In a preferred embodiment, the anti-CTLA4 antibody is a human anti-CTLA4 antibody. A preferred human anti-CTLA4 antibody of the invention is 10D1, but the methods of the present invention can be used with any human CTLA-4 antibody. In other embodiments, the anti-CTLA4 antibody is a recombinant antibody such as a chimeric or humanized (e.g., CDR-grafted) anti-CTLA4 antibody.

The antibodies of the invention also can be used in the control of pathogenic infections by infectious organisms, including, but not limited to, bacteria, mycobacteria, spirochetes, fungi, viruses, parasitic organisms, and prions. The antibodies can be used as a single agent or in combination with one or more other agents, such as antibiotics, vaccines, antibodies, cytokines, receptor inhibitors, and virulence blocking agents. The antibodies can be administered as a single dose or as multiple doses.

The methods of treatment of the invention, which are designed to stimulate a secondary or memory immune response, may be particularly relevant in the treatment of immune suppressed patients who could be at a high risk for complications of disease. Examples of such immune suppressed patients include patients with retroviral infections, including HIV, patients with congenital, inherited, autoimmune or pharmaceutically-induced immune deficiencies, including diabetic and elderly patients, and patients with wounds, trauma or severe burns.

The method of the invention for stimulating an immune response by administering an anti-CTLA4 antibody also can be used in cases of acute exposure to the antigen (such as exposure to a bioterrorism agent, such as anthrax or smallpox, wherein the exposed patient has been previously vaccinated against the agent), or in place of booster vaccination.

The invention also demonstrates that patients can be treated for extended periods of time with anti-CTLA4 without experiencing detrimental side effects such as non-specific T cell activation, such as autoimmunity.

Plasma concentrations of anti-CTLA4 can be maintained above detectable levels for at least 1, 2, 3, 4 or 5 months, or longer, without unintended immunological consequences. In a preferred embodiment, the invention provides a method for inducing or enhancing an immune response to an antigen in a patient, comprising administering to the patient an anti-CTLA4 antibody such that the plasma concentration of the anti-CTLA4 antibody is maintained above detectable levels for at least one, two, three, four or five months. In one embodiment, the anti-CTLA4 antibody is administered multiple times such that the plasma concentration is maintained above detectable levels for at least one, two, three, four or five months. In another embodiment, the anti-CTLA4 antibody is administered in an amount and at intervals such that the plasma concentration of anti-CTLA4 antibody in the patient is at least 2 µg/ml for at least one, two, three, four or five months. In another embodiment, the anti-CTLA4 antibody is administered in an amount and at intervals such that the plasma concentration of anti-CTLA4 antibody in the patient is at least 5 µg/ml for at least one, two, three, four or five months. In another embodiment, the anti-CTLA4 antibody is administered in an amount and at intervals such that the plasma concentration of anti-CTLA4 antibody in the patient is at least 10 µg/ml for at least one, two, three, four or five months. In a preferred embodiment, the patient being treated for extended periods of time with the anti-CTLA4 antibody is suffering from a malignancy, such as melanoma or prostate cancer. In another preferred embodiment, the patient has been, or is being, treated with a vaccine in addition to treatment with the anti-CTLA4 antibody.

Another aspect of the invention pertains to methods of using anti-CTLA4 antibodies that are linked to a cytotoxic agent. Examples of cytotoxic agents include cytotoxic drugs (e.g., doxirubicin, calicheamycin and the like) and radioactive isotopes. Such anti-CTLA-4 antibodies linked to a cytotoxic agent can be used to deplete CTLA4$^+$ cells. Examples of CTLA4+ cells that can be deleted include CTLA4$^+$ malignancies and antigen-specific activated T cells expressing CTLA4 in T cell mediated autoimmune diseases. Accordingly, in another embodiment, the invention provides a method for treating a patient for a CTLA4$^+$ T cell malignancy, comprising: administering to the patient an anti-CTLA4 antibody linked to a cytotoxic agent such that the patient is treated for the T cell malignancy. In another embodiment, the invention provides a method for treating a patient for a T cell mediated autoimmune disease, comprising: administering to the patient an anti-CTLA4 antibody linked to a cytotoxic agent such that the patient is treated for the T cell mediated autoimmune disease.

In a preferred embodiment, the anti-CTLA-4 antibody of the present invention is human monoclonal antibody 10D1 as disclosed in WO 01/14424. The 10D1 antibody comprises a heavy chain variable region that comprises CDR1, CDR2, and CDR3 domains; and a light chain variable region that comprises CDR1, CDR2, and CDR3 domains, wherein the heavy chain variable region CDR1 comprises amino acids having the sequence set forth in SEQ ID NO:3; the heavy chain variable region CDR2 comprises amino acids having the sequence set forth in SEQ ID NO:4; the heavy chain variable region CDR3 comprises amino acids having the sequence set forth in SEQ ID NO:5; the light chain variable region CDR1 comprises amino acids having the sequence set forth in SEQ ID NO:6; the light chain variable region CDR2 comprises amino acids having the sequence set forth in SEQ ID NO:7; and the light chain variable region CDR3 comprises amino acids having the sequence set forth in SEQ ID NO:8. The 10D1 antibody comprises a heavy chain variable region comprising amino acids comprising the sequence set forth in SEQ ID NO:9. The 10D1 antibody comprises a light chain variable region comprising amino acids comprising the sequence set forth in SEQ ID NO:10. All publications, figures, GenBank Accession references (sequences), ATCC Deposits, patents and patent applications cited herein are hereby expressly incorporated by reference for all purposes to the same extent as if each was so individually denoted.

DETAILED DESCRIPTION

Figure 1:
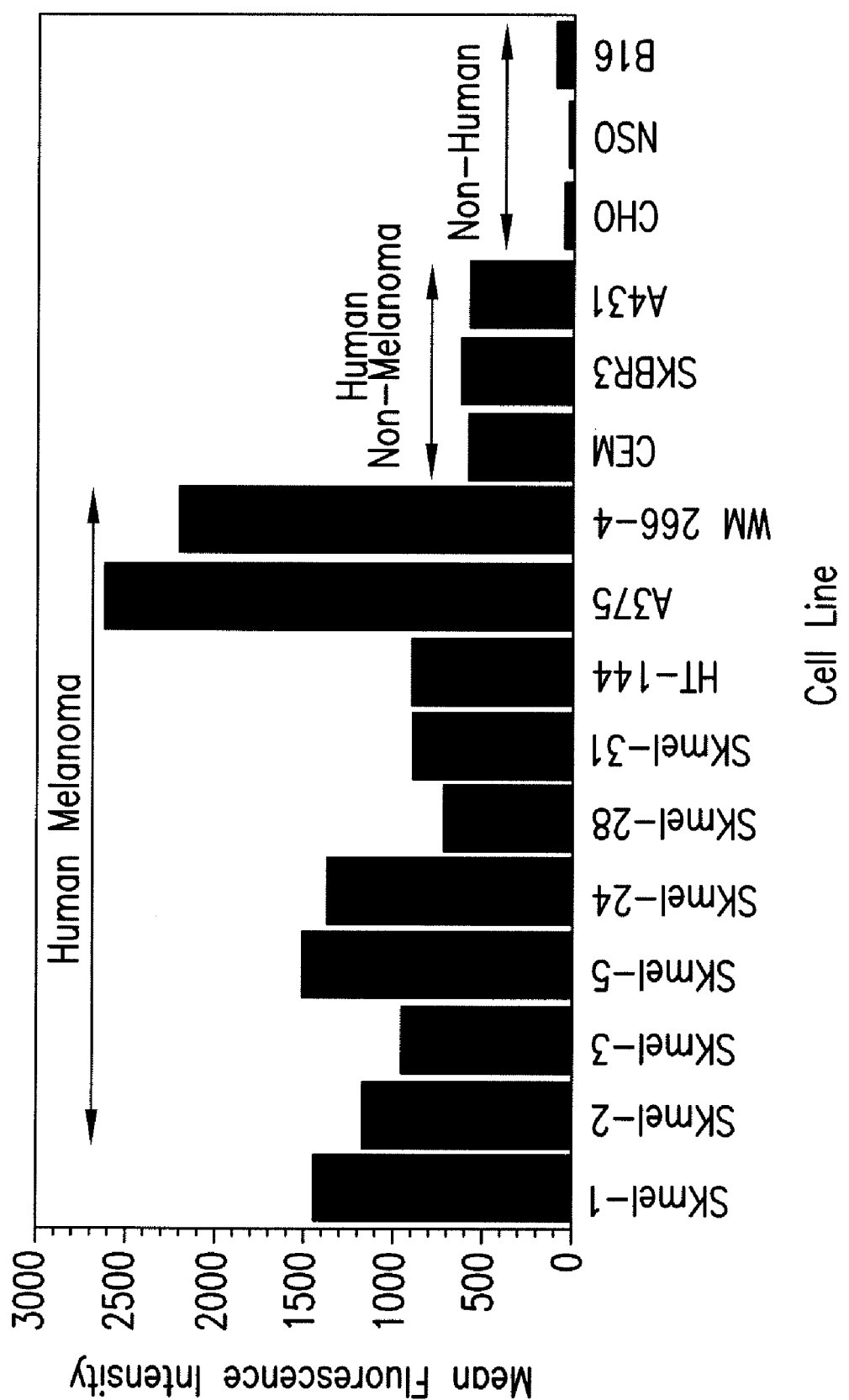
FIG. 1 shows melanoma-specific antibody responses in animals treated with a melanoma vaccine and the anti-CTLA-4 antibody 10D1. Antibody reactivity in pooled plasma samples from treated animals was measured by flow cytometry.

The present invention provides novel CTLA-4 antibody-based methods for promoting or potentiating a secondary or memory immune response, and for more effective cancer treatment. In addition, preferred plasma concentrations of anti-CTLA-4 antibody are disclosed. The methods of the present invention provide means for treating cancer, infection, and other diseases or conditions that are responsive to an immune response.

The present invention is based, in part, on observations made during clinical testing of a human sequence anti-CTLA-4 antibody in immunotherapy of cancers, as described below. The tests demonstrate the effectiveness of anti-CTLA antibody in the treatment of subjects with previous exposure to tumor antigen. Furthermore, the persistence of detectable plasma levels of anti-CTLA-4 antibody following either single or multiple administrations is shown.

A. Clinical Testing of Patients Previously Vaccinated with Cancer Vaccine

Nine patients with advanced melanoma or advanced ovarian cancer participated in a study in which they received 3 mg/kg of CTLA-4 monoclonal antibody 10D1 (Medarex) intravenously. The patients received prior treatment for early stage melanoma that included immunotherapy (three patients received a-interferon, one patient received a vaccine of GM2 ganglioside admixed with QS-21), surgery (4 patients), radiation (2 patients), chemotherapy (3 patients), and proteasome inhibitor (1 patient). The two ovarian cancer patients had received multiple chemotherapies. In addition, all patients participated in Phase I vaccine studies. Three melanoma and both ovarian cancer patients were immunized with autologous cells engineered to secrete GM-CSF. One of these patients also received a MUC-1 vaccine.

Three melanoma patients were immunized with autologous dendritic cells engineered to express gp100 and MART-I. One melanoma patient was vaccinated with gp100 peptide and high-dose IL-2. Three melanoma patients previously vaccinated with GM-CSF secreting tumor cells had extensive tumor necrosis following treatment with 10D1. Histopathology resected tissue from all three patients showed severely damaged tumor blood vessels with lymphocyte and granulocyte infiltrates in proximity to the tumor. One patient had a mediastinal mass completely resected three months after treatment with 10D1. The four patients previously vaccinated with melanosomal antigens had lymphocytic infiltrates in proximity to the tumors, but no tumor necrosis. The ovarian cancer patients did not undergo resection or biopsy, but both patients had favorable changes in CA-125 (a tumor marker for ovarian cancer) blood levels following 10D1 treatment.

B. Testing of Patients with Natural Exposure to Tumor Antigen

Fourteen patients with Stage 1V melanoma received anti-CTLA-4 antibody 10D1 in conjunction with vaccination with two gp100 peptides in one or more treatment cycles. All patients had prior surgery for their primary tumor. Six patients had prior chemotherapy. Eleven patients had prior immunotherapy. Clinical response was measured by computed axial tomography (CT) and magnetic resonance (MR) imaging. One patient, who had prior surgery and chemotherapy, had complete resolution of lung, brain and subcutaneous tumors after 5 treatment cycles. Two other patients were partial responders. Two patients were "mixed" non-responders because some lesions shrunk while others increased in size. It is possible, because tissue biopsies were not performed, that the enlargement of lesions in the mixed non-responders was not due to cancer. One patient (Patient 3), for example, had resolution of several lung lesions but an enlargement of mediastinal lymph nodes. Lymphatic vessels from the lungs drain into mediastinal lymph nodes (Schwartz, et al., Principles of Surgery, 1984, 4th ed., p. 661); and lymph nodes can enlarge as a result of inflammation in the tissues within the drainage basin of the lymph nodes. It is possible that Patient 3 was a complete responder with lymph nodes that enlarged due to inflammation, not due to cancer.

Based on the results discussed above, the present invention provides a number of advantageous uses of anti-CTLA-4 antibodies. These antibodies provide for secondary or memory immune stimulation, as demonstrated in the previously immunized or exposed cancer patients. Thus, anti-CTLA-4 antibodies can be used as a booster, which is especially useful in immunocompromised patients. Immune system suppression can occur from a number of causes, including but not limited to illness (including immunodeficiency diseases like HIV), aging, increased tumor burden, cancer therapy (e.g., chemotherapy and radiation), as well as other causes. Anti-CTLA-4 antibody therapy is thus indicated to boost immunity in immunocompromised subjects.

C. Testing of Monkeys with CTLA-4 Antibody and Melanoma Vaccine

Cynomolgus monkeys were treated with either melanoma vaccine alone or melanoma vaccine and anti-CTLA-4 antibody 10D1 on days 0, 28, 56, 84 and 140. Use of the anti-CTLA-4 antibody in combination with the vaccine resulted in a significantly greater antibody response against melanoma cells than use of the vaccine alone. Moreover, T cell proliferation studies demonstrated that treatment with anti-CTLA-4 antibody and vaccine resulted in antigen-specific proliferation of $CD8^+$ and $CD4^+$ cells. Plasma levels of the anti-CTLA-4 antibody remained above detectable levels for the entire 160 day period. The mean plasma concentration remained above 20 µg/ml during the six month study.

This study showed that chronic dosing of anti-CTLA-4 antibody in primates is safe and that detectable plasma levels can be maintained over a six month period.

D. Testing of Advanced Melanoma Patients with Anti-CTLA-4 Antibody

Seventeen patients with advanced melanoma were administered a single dose of anti-CTLA-4 antibody 10D1 at 3 mg/kg intravenously. Nine patients had prior immunotherapy, six had prior radiation therapy and five had prior chemotherapy. Plasma levels of anti-CTLA-4 antibody remained detectable for up to four months. Two patients had a partial response, including resolution of three soft tissue masses and a greater than 50% reduction in a lung mass in a previously vaccinated patient.

This study showed that plasma levels can remain above detectable levels for up to four months in a human patient following a single dose of anti-CTLA-4 antibody. Furthermore, the reduction of the lung mass seen in the previously vaccinated patient demonstrated that CTLA-4 antibody can activate a pre-existing memory response to the tumor.

E. Testing of Advanced Prostate Cancer Patients with Anti-CTLA-4 Antibody

Fourteen patients with advanced prostate cancer were administered a single dose of human monoclonal anti-CTLA-4 antibody 10D1 at 3.0 mg/kg intravenously. Plasma levels of the anti-CTLA-4 antibody were present for up to four months. Reductions in prostate specific antigen (PSA) and symptomatic relief were noted. With the exception of rash and pruritus, which were reversible, there were no adverse immune effects.

These and other advantages of the invention are explained in greater detail below and in the Examples.

Except when noted, the terms "patient" or "subject" are used interchangeably and refer to mammals such as human patients and non-human primates, as well as experimental animals such as rabbits, rats, and mice, and other animals. Animals include all vertebrates, e.g., mammals and non-mammals, such as sheep, dogs, cows, chickens, amphibians, and reptiles.

The term "treating" includes the administration of the compounds or agents of the present invention to prevent or delay the onset of the symptoms, complications, or biochemical indicia of a disease, alleviating the symptoms or arresting or inhibiting further development of the disease, condition, or disorder (e.g., autoimmune disease). Treatment may be prophylactic (to prevent or delay the onset of the disease, or to prevent the manifestation of clinical or subclinical symptoms thereof) or therapeutic suppression or alleviation of symptoms after the manifestation of the disease.

The term "advanced cancer" means cancer that is no longer localized to the primary tumor site, or a cancer that is Stage III or IV according to the American Joint Committee on Cancer (AJCC).

In general, the phrase "well tolerated" refers to the absence of adverse changes in health status that occur as a result of the treatment and would affect treatment decisions.

The term "lymphocyte" as used herein has the normal meaning in the art, and refers to any of the mononuclear, nonphagocytic leukocytes, found in the blood, lymph, and lymphoid tissues, i.e., B and T lymphocytes.

The phrase "subpopulations of T lymphocytes" or "T cell subset(s)" refers to T lymphocytes or T cells characterized by the expression of particular cell surface markers (see Barclay, A. N. et al. (eds.), 1997, The Leukocyte Antigen Facts Book, 2nd. edition, Academic Press, London, United Kingdom). The term "stable" in reference to T cells refers to the fact that the frequency or percentage of a T cell subset does not change over the course or duration of the administration of an agent.

The terms "cytotoxic T lymphocyte-associated antigen-4," "CTLA-4," "CTLA4," "CTLA-4 antigen" and "CD152" (see, e.g., Murata (1999) Am. J. Pathol. 155:453-460) are used interchangeably, and include variants, isoforms, species homologs of human CTLA-4, and analogs having at least one common epitope with CTLA-4 (see, e.g., Balzano (1992) Int. J. 5 Cancer Suppl. 7:28-32). CTLA-4's complete sequence is found in GenBank Accession No. L15006.

The term "epitope" means a protein determinant capable of specific binding to an antibody. Epitopes usually consist of chemically active surface groupings of molecules such as amino acids or sugar side chains and usually have specific three dimensional structural characteristics, as well as specific charge characteristics. Conformational and nonconformational epitopes are distinguished in that the binding to the former but not the latter is lost in the presence of denaturing solvents.

An intact "antibody" comprises at least two heavy (H) chains and two light (L) chains inter-connected by disulfide bonds. Each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region.

The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxyl-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system. The term antibody includes antigen-binding portions of an intact antibody that retain capacity to bind CTLA-4. Examples of binding include (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341 :544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); See, e.g., Bird et al. (1988) *Science* 242:423-426; and Huston et al. (1988) *Proc. Natl. Acad. Sci. USA* 85:5879-5883). Such single chain antibodies are included by reference to the term "antibody" Fragments can be prepared by recombinant techniques or enzymatic or chemical cleavage of intact antibodies.

The term "human sequence antibody" includes antibodies having variable and constant regions (if present) derived from human germline immunoglobulin sequences. The human sequence antibodies of the invention may include amino acid residues not encoded by human germline immunoglobulin sequences (e.g., mutations introduced by random or site-specific mutagenesis in vitro or by somatic mutation in vivo). Such antibodies can be generated in non-human transgenic animals, i.e., as described in PCT Publication Nos. WO 01/14424 and WO 00/37504. However, the term "human sequence antibody", as used herein, is not intended to include antibodies in which CDR sequences derived from the germline of another mammalian species, such as a mouse, have been grafted onto human framework sequences (i.e., humanized antibodies).

The terms "monoclonal antibody" or "monoclonal antibody composition" refer to a preparation of antibody molecules of single molecular composition. A monoclonal antibody composition displays a single binding specificity and affinity for a particular epitope. Accordingly, the term "human monoclonal antibody" refers to antibodies displaying a single binding specificity which have variable and constant regions (if present) derived from human germline immunoglobulin sequences. In one embodiment, the human monoclonal antibodies are produced by a hybridoma which includes a B cell obtained from a transgenic non-human animal, e.g., a transgenic mouse, having a genome comprising a human heavy chain transgene and a light chain transgene fused to an immortalized cell.

The term "polyclonal antibody" refers to a preparation of more than 1 (two or more) different antibodies to human CTLA-4. Such a preparation includes antibodies binding to a range of different epitopes.

CTLA-4 antibodies can bind to an epitope on human CTLA-4 so as to inhibit CTLA-4 from interacting with a human B7 counterreceptor. Because interaction of human CTLA-4 with human B7 transduces a signal leading to inactivation of T-cells bearing the human CTLA-4 receptor, antagonism of the interaction effectively induces, augments or prolongs the activation of T cells bearing the human CTLA-4 receptor, thereby prolonging or augmenting an immune response. Preferred anti-CTLA-4 antibodies are described, for example, in U.S. Pat. Nos. 5,811,097; 5,855, 887; 6,051,227; in PCT Publication Nos. WO 01/14424 and WO 00/37504; and in U.S. Publication No. 2002/0039581 A1. These and other antibodies suitable for use in the present invention can be prepared according to methods that are well known in the art and/or are described in the references cited here. In preferred embodiments, anti-CTLA-4 antibodies used in the invention are "human antibodies"—i.e., antibodies isolated from a human—or they are "human sequence antibodies" (defined supra). For example, International Patent Publication number WO 01/14424 describes methods by which human sequence anti-CTLA-4 antibodies are isolated from a transgenic mouse that has been modified with human antibody genes. These antibodies, therefore, although isolated from a non-human animal, have amino acid sequences (including constant and variable domain sequences) that correspond to these of a human antibody. A particularly preferred antibody, which is used in the Examples, infra, is referred to here as the antibody 10D1. This human sequence antibody has been previously described and is fully characterized, e.g., in WO 01/14424.

The phrase "immune cell response" refers to the response of immune system cells to external or internal stimuli (e.g., antigen, cytokines, chemokines, and other cells) producing biochemical changes in the immune cells that result in immune cell migration, killing of target cells, phagocytosis, production of antibodies, other soluble effectors of the immune response, and the like.

The terms "T lymphocyte response" and "T lymphocyte activity" are used here interchangeably to refer to the component of immune response dependent on T lymphocytes (i.e., the proliferation and/or differentiation of T lymphocytes into helper, cytotoxic killer, or suppressor T lymphocytes, the provision of signals by helper T lymphocytes to B lymphocytes that cause or prevent antibody production, the killing of specific target cells by cytotoxic T lymphocytes, and the release of soluble factors such as cytokines that modulate the function of other immune cells).

The term "immune response" refers to the concerted action of lymphocytes, antigen presenting cells, phagocytic cells, granulocytes, and soluble macromolecules produced by the above cells or the liver (including antibodies, cytokines, and complement) that results in selective damage to, destruction of, or elimination from the human body of invading pathogens, cells or tissues infected with pathogens, cancerous cells, or, in cases of autoimmunity or pathological inflammation, normal human cells or tissues.

Components of an immune response may be detected in vitro by various methods that are well known to those of ordinary skill in the art. For example, (1) cytotoxic T lymphocytes can be incubated with radioactively labeled target cells and the lysis of these target cells detected by the release of radioactivity, (2) helper T lymphocytes can be incubated with antigens and antigen presenting cells and the synthesis and secretion of cytokines measured by standard methods (Windhagen A; et al., 1995, Immunity 2(4): 373-80), (3) antigen presenting cells can be incubated with whole protein antigen and the presentation of that antigen on MHC detected by either T lymphocyte activation assays or biophysical methods (Harding et al., 1989, 15 Proc. Natl. Acad. Sci., 86: 4230-4), (4) mast cells can be incubated with reagents that cross-link their Fe-epsilon receptors and histamine release measured by enzyme immunoassay (Siraganian, et al., 1983, TIPS 4: 432-437).

Similarly, products of an immune response in either a model organism (e.g., mouse) or a human patient can also be detected by various methods that are well known to those of ordinary skill in the art. For example, (1) the production of antibodies in response to vaccination can be readily detected by standard methods currently used in clinical laboratories, e.g., an ELISA; (2) the migration of immune cells to sites of inflammation can be detected by scratching the surface of skin and placing a sterile container to capture the migrating cells over scratch site (Peters et al., 1988, Blood 72: 1310-5); (3) the proliferation of peripheral blood mononuclear cells in response to mitogens or mixed lymphocyte reaction can be measured using 3H-thymidine; (4) the phagocitic capacity of granulocytes, macrophages, and other phagocytes in PBMCs can be measured by placing PMBCs in wells together with labeled particles (Peters et al., 1988); and (5) the differentiation of immune system cells can be measured by labeling PBMCs with antibodies to CD molecules such as CD4 and CD8 and measuring the fraction of the PBMCs expressing these markers.

For convenience, immune responses are often described in the present invention as being either "primary" or "secondary" immune responses. A primary immune response, which is also described as a "protective" immune response, refers to an immune response produced in an individual as a result of some initial exposure (e.g. the initial "immunization") to a particular antigen. Such an immunization may occur, for example, as the result of some natural exposure to the antigen (for example, from initial infection by some pathogen that exhibits or presents the antigen) or from antigen presented by cancer cells of some tumor in the individual (for example, a resected tumor). Alternatively, the immunization may occur as a result of vaccinating the individual with a vaccine containing the antigen. For example, the vaccine may be a vaccine against a particular pathogen (for example, against a virus, a bacterium, or a parasite) or it may be a cancer vaccine comprising one or more antigens from a cancer cell.

A primary immune response may become weakened or attenuated over time and may even disappear or at least become so attenuated that it cannot be detected. Accordingly, the present invention also relates to a "secondary" immune response, which is also described here as a "memory immune response." The term secondary immune response refers to an immune response elicited in an individual after a primary immune response has already been produced. Thus, a secondary or immune response may be elicited, e.g. to enhance an existing immune response that has become weakened or attenuated, or to recreate a previous immune response that has either disappeared or can no longer be detected. An agent that can be administrated to elicit a secondary immune response is after referred to as a "booster" since the agent can be said to "boost" the primary immune response.

As an example, and not by way of limitation, a secondary immune response can be elicited by re-introducing to the individual an antigen that elicited the primary immune response (for example, by re-administrating a vaccine). However, a secondary immune response to an antigen can also be elicited by administrating other agents that may not contain the actual antigen. For example, the present invention provides methods for potentiating a secondary immune response by administrating an anti-CTLA-4 antibody to an individual. In such methods the actual antigen need not necessarily be administered with the anti-CTLA-4 antibody and the composition containing the anti-CTLA-4 antibody need not necessarily contain the antigen. The secondary or memory immune response can be either a humoral (antibody) response or a cellular response. A secondary or memory humoral response occurs upon stimulation of memory B cells that were generated at the first presentation of the antigen. Delayed type hypersensitivity (DTH) reactions are a type of cellular secondary or memory immune response that are mediated by CD4+ cells. A first exposure to an antigen primes the immune system and additional exposure(s) results in a DTH.

As used herein, the phrase "cell surface receptor" includes molecules and complexes of molecules capable of receiving a signal and the transmission of such a signal across the plasma membrane of a cell. An example of a "cell surface receptor" of the present invention is the T cell receptor (TCR) or the B7 ligands of CTLA-4.

The term "nonspecific T cell activation" refers to the stimulation of T cells independent of their antigenic specificity.

As used herein, the term "effector cell" refers to an immune cell which is involved in the effector phase of an immune response, as opposed to the cognitive and activation phases of an immune response. Exemplary immune cells include a cell of a myeloid or lymphoid origin, e.g., lymphocytes (e.g., B cells and T cells including cytolytic T cells (CTLs)), killer cells, natural killer cells, macrophages, monocytes, eosinophils, neutrophils, polymorphonuclear cells, granulocytes, mast cells, and basophils. Effector cells express specific Fe receptors and carry out specific immune functions. An effector cell can induce antibody-dependent cell-mediated cytotoxicity (ADCC), e.g., a neutrophil capable of inducing ADCC. For example, monocytes, macrophages, neutrophils, eosinophils, and lymphocytes which express FcαR are involved in specific killing of target cells and presenting antigens to other components of the immune system, or binding to cells that present antigens. An effector cell can also phagocytose a target antigen, target cell, or microorganism.

"Target cell" shall mean any undesirable cell in a subject (e.g., a human or animal) that can be targeted by a composition (e.g., a human sequence antibody or a human monoclonal antibody of the invention, a bispecific or a multispecific molecule of the invention). The target cell can be a cell expressing or overexpressing human CTLA-4. Cells expressing human CTLA-4 can include tumor cells, e.g. lymphomas.

Also included in the invention are modified antibodies. The term "modified antibody" includes antibodies, such as monoclonal antibodies, chimeric antibodies, and humanized antibodies which have been modified by, e.g., deleting, adding, or substituting portions of the antibody. For example, an antibody can be modified by deleting the constant region and replacing it with a constant region meant to increase half-life, e.g., serum half-life, stability or affinity of the antibody.

The antibody conjugates of the invention can be used to modify a given biological response or create a biological response (e.g., to recruit effector cells). The drug moiety is not to be construed as limited to classical chemical therapeutic agents. For example, the drug moiety may be a protein or polypeptide possessing a desired biological activity. Such proteins may include, for example, an enzymatically active toxin, or active fragment thereof, such as abrin, ricin A, pseudomonas exotoxin, or diphtheria toxin; a protein such as tumor necrosis factor or interferon-alpha; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Techniques for conjugating such therapeutic moiety to antibodies are well known, see, e.g., Amon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev., 62:119-58 (1982).

Cancer Treatment

Blockade of CTLA-4 by antibodies can enhance the memory or secondary immune response to cancerous cells in the patient. Antibodies to CTLA-4 can be combined with an immunogenic agent, such as cancerous cells, purified tumor antigens (including recombinant proteins, peptides, and carbohydrate molecules), cells, and cells transfected with genes encoding immune stimulating cytokines and cell surface antigens such as B7 (see, e.g., Hurwitz, A. et al. (1998) Proc. Natl. Acad. Sci U.S.A. 1998; 95:10067-10071), or used alone, to stimulate immunity.

CTLA-4 blockade is effective when following a vaccination protocol. Many experimental strategies for vaccination against tumors have been devised (see Rosenberg, S., 2000, Development of Cancer Vaccines, ASCO Educational Book Spring: 60-62; Logothetis, c., 2000, ASCO Educational Book Spring: 300-302; Khayat, D. 2000, ASCO Educational Book Spring: 414-428; Foon, K. 2000, ASCO Educational Book Spring: 730-738; see also Restifo, N. and Sznol, M., Cancer Vaccines, Ch. 61, pp. 3023-3043 in DeVita, V. et al. (eds.), 1997, Cancer: Principles and Practice of Oncology, Fifth Edition). In one of these strategies, a vaccine is prepared using autologous or allogeneic tumor cells. These cellular vaccines have been shown to be most effective when the tumor cells are transduced to express GM-CSF. GM-CSF has been shown to be a potent activator of antigen presentation for tumor vaccination (Dranoff et al. Proc. Natl. Acad. Sci U.S.A. 1993; 90: 3539-43).

Anti-CTLA-4 blockade to boost GM-CSF-modified tumor cell vaccines improves efficacy of vaccines in a number of experimental tumor models such as mammary carcinoma (Hurwitz et al., 1998, supra), primary prostate cancer (Hurwitz et al., Cancer Research 2000; 60:2444-8) and melanoma (van Elsas et al. 1. Exp. Med. 1999, 190:355-66). In these instances, non-immunogenic tumors, such as the B16 melanoma, have been rendered susceptible to destruction by the immune system. The tumor cell vaccine may also be modified to express other immune activators such as IL-2, and costimulatory molecules, among others.

The study of gene expression and large scale gene expression patterns in various tumors has led to the definition of so called "tumor specific antigens" (Rosenberg, Immunity 1999; 10:281-7). In many cases, these tumor specific antigens are differentiation antigens expressed in the tumors and in the cell from which the tumor arose, for example melanocyte antigens gp100, MAGE antigens, Trp-2. More importantly, many of these antigens can be shown to be the targets of tumor specific T cells found in the host. CTLA-4 blockade may be used as a boosting agent in conjunction with vaccines based on recombinant versions of proteins and/or peptides found to be expressed in a tumor in order to potentiate a secondary or memory immune response to these proteins. These proteins are normally viewed by the immune system as self antigens and are therefore tolerant to them. The tumor antigen may also include the protein telomerase, which is required for the synthesis of telomeres of chromosomes and which is expressed in more than 85% of human cancers and in only a limited number of somatic tissues (Kim et al., Science 1994; 266:2011-2013). These somatic tissues may be protected from immune attack by various means. Tumor antigen may also be "neo-antigens" expressed in cancer cells because of somatic mutations that alter protein sequence or create fusion proteins between two unrelated sequences (i.e. bcr-abl in the Philadelphia chromosome), or idiotype from B cell tumors. Other tumor vaccines may include the proteins from viruses implicated in human cancers such a Human Papilloma Viruses (HPV), Hepatitis Viruses (HBV and HCV) and Kaposi's Herpes Sarcoma Virus (KHSV). Another form of tumor specific antigen which may be used in conjunction with CTLA-4 blockade is purified heat shock proteins (HSP) isolated from the tumor tissue itself. These heat shock proteins contain fragments of proteins from the tumor cells and these HSPs are highly efficient at delivery to antigen presenting cells for eliciting tumor immunity (Soot and Srivastava, Science 1995; 269:1585-1588; Tamura et al., Science 1997, 278: 117-120).

Dendritic cells (DC) are potent antigen presenting cells that can be used to prime antigen-specific responses. DC's can be produced ex vivo and loaded with various protein and peptide antigens as well as tumor cell extracts (Nestle et al., Nature Medicine 1998; 4:328-332). DCs may also be transduced by genetic means to express these tumor antigens as well. DCs have also been fused directly to tumor cells for the purposes of immunization (Kugler et al., Nature Medicine 2000; 6:332-336). As a method of vaccination, DC immunization may be 20 effectively boosted with CTLA-4 blockade to activate more potent anti-tumor responses.

Another type of melanoma vaccine that can be combined with CTLA-4 blockade is a vaccine prepared from a melanoma cell line lysate, in conjunction with an immunological adjuvant, such as the MELACINE® vaccine, a mixture of lysates from two human melanoma cell lines plus DETOX™ immunological adjuvant. Vaccine treatment can be boosted with anti-CTLA-4, with or without additional chemotherapeutic treatment. CTLA-4 blockade may also be used to boost immunity induced through standard cancer treatments. In these instances, it may be possible to reduce the dose of chemotherapeutic reagent administered (Mokyr et al., Cancer Research, 1998; 58:5301-5304). The scientific rationale behind the combined use of CTLA-4 blockade and chemotherapy is that cell death, that is a consequence of the cytotoxic action of most chemotherapeutic compounds, should result in increased levels of tumor antigen in the antigen presentation pathway. Thus, CTLA-4 can boost an immune response primed to chemotherapy release of tumor cells. Moreover, the immunostimulatory activity of CTLA-4 is useful to overcome the immunosuppressive effects of chemotherapy. Examples of chemotherapeutic agents with which anti-CTLA-4 treatment can be combined include, but are not limited to, aldesleukin, altretamine, amifostine, asparaginase, bleomycin, capecitabine, carboplatin, carmustine, cladribine, cisapride, cisplatin, cyclophosphamide, cytarabine, dacarbazine (DTIC), dactinomycin, docetaxel, doxorubicin, dronabinol, epoetin alpha, etoposide, filgrastim, fludarabine, fluorouracil, gemcitabine, granisetron, hydroxyurea, idarubicin, ifosfamide, interferon alpha, irinotecan, lansoprazole, levamisole, leucovorin, megestrol, mesna, methotrexate, metoclopramide, mitomycin, mitotane, mitoxantrone, omeprazole, ondansetron, paclitaxel (Taxol®), pilocarpine, prochloroperazine, rituximab, tamoxifen, taxol, topotecan hydrochloride, trastuzumab, vinblastine, vincristine and vinorelbine tartrate. For prostate cancer treatment, a preferred chemotherapeutic agent with which anti-CTLA-4 can be combined is paclitaxel (Taxol®). For melanoma cancer treatment, a preferred chemotherapeutic agent with which anti-CTLA-4 can be combined is dacarbazine (DTIC).

Other combination therapies that may result in immune system priming through cell death are radiation, surgery, and hormone deprivation (Kwon, E. et al. Proc. Natl. Acad. Sci U.S.A. 1999; 96 (26): 15074-9. Each of these protocols creates a source of tumor antigen in the host. For example, any manipulation of the tumor at the time of surgery can greatly increase the number of cancer cells in the blood (Schwartz, et al., Principles of Surgery 1984. 4th ed. p. 338). Angiogenesis inhibitors may also be combined with CTLA-4 blockade. Inhibition of angiogenesis leads to tumor cell death which may feed tumor antigen into host antigen presentation pathways. All of these cause tumor release and possible immune system priming that CTLA-4 blockage can boost.

Infectious Diseases

Other methods of the invention are used to treat patients that have been exposed to particular toxins or pathogens. Similar to its application to tumors as discussed above, antibody mediated CTLA-4 blockade can be used alone, or as an adjuvant, in combination with vaccines, to stimulate the secondary or memory immune response to pathogens, toxins, and self-antigens. CTLA-4 blockade has been shown to be effective in the acute phase of infections of *Nippostrongylus brasiliensis* (McCoy, K. et al. (1997) 186(2); 183-187) and *Leishmania donovani* (Murphy, M. et al. (1998) 1. Immunol. 161:4153-4160). Examples of pathogens for which this therapeutic approach may be particularly useful include pathogens for which there is currently no effective vaccine, or pathogens for which conventional vaccines are less than completely effective. These include, but are not limited to HIV, Hepatitis (A, B, & C), Influenza, Herpes, *Giardia*, Malaria, *Leishmania*, *Staphylococcus aureus*, and *Pseudomonas aeruginosa*. CTLA-4 blockade is particularly useful in boosting immunity against established infections by agents such as HIV that present altered antigens over the course of the infections. These novel epitopes are recognized as foreign at the time of anti-human CTLA-4 administration, thus provoking a strong T cell response that is not dampened by negative signals through CTLA-4.

Some examples of pathogenic viruses causing infections treatable by methods of the invention include hepatitis (A, B, or C), herpes virus (e.g., VZV, HSV-1, HAV-6, HSV-II, and CMV, Epstein Barr virus), adenovirus, influenza virus, flaviviruses, echovirus, rhinovirus, coxsackie virus, cornovirus, respiratory syncytial virus, mumps virus, rotavirus, measles virus, rubella virus, parvovirus, vaccinia virus, HTLV virus, dengue virus, papillomavirus, molluscum virus, poliovirus, rabies virus, JC virus and arboviral encephalitis virus.

Some examples of pathogenic bacteria causing infections treatable by methods of the invention include chlamydia, rickettsial bacteria, mycobacteria, staphylococci, streptococci, pneumonococci, meningococci and conococci, *klebsiella, proteus, serratia*, pseudomonas, *legionella*, diphtheria, *salmonella*, bacilli, cholera, tetanus, botulism, anthrax, plague, leptospirosis, and Lyme disease bacteria.

Some examples of pathogenic fungi causing infections treatable by methods of the invention include *Candida (albicans, krusei, glabrata, tropicalis*, etc.), *Cryptococcus neoformans, Aspergillus (fumigatus, niger*, etc.), Genus Mucorales *(Mucor, Absidia, Rhizophus), Sporothrix schenkii, Blastomyces dermatitidis, Paracoccidioides brasiliensis, Coccidioides immitis* and *Histoplasma capsulatum*.

Some examples of pathogenic parasites causing infections treatable by methods of the invention include *Entamoeba histolytica, Balantidium coli, Naegleria fowleri, Acanthamoeba* sp., *Giardia lambia, Cryptosporidium* sp., *Pneumocystis carinii, Plasmodium vivax, Babesia microti, Trypanosoma brucei, Trypanosoma cruzi, Leishmania donovani, Toxoplasma gondi, Nippostrongylus brasiliensis*.

Promoting Beneficial "Autoimmune" Reactions

The ability of anti-CTLA-4 antibodies to provoke and amplify autoimmune responses has been documented in a number of experimental systems (EAE—Experimental Autoimmune Encephalomyelitis, a murine model for MS (Perrin et al., J Immunol 1996; 157:1333-1336); diabetes (Luhder et al., 1998, supra). Indeed, induction of anti-tumor responses using tumor cell and peptide vaccines reveals that many anti-tumor responses involve anti-self reactivities (depigmentation observed in anti-CTLA-4+GM-CSF modified B16 melanoma in van Elsas et al. supra; depigmentation in Trp-2 vaccinated mice (Overwijk et al., Proc. Natl. Acad. Sci. U.S.A. 1999 96:2982-2987); autoimmune prostatitis evoked by TRAMP tumor cell vaccines (Hurwitz 2000, supra), melanoma peptide antigen vaccination and vitiligo observed in human clinical trials (Rosenberg and White, J Immunother Emphasis Tumor Immunol 1996; 19: 81-4).

Therefore, it is possible to consider using anti-CTLA-4 boosting in conjunction with various self-proteins in order to devise vaccination protocols to efficiently generate immune responses against these self-proteins for disease treatment. For example, Alzheimer's disease involves inappropriate accumulation of Aβ peptide in amyloid deposits in the brain; antibody responses against amyloid are able to clear these amyloid deposits (Schenk et al., Nature 1999; 400: 173-177).

Other self-proteins may also be used as targets such as IgE for the treatment of allergy and asthma, and TNF for rheumatoid arthritis. Finally, antibody responses to various hormones may be induced by the use of anti-CTLA-4 antibody. Neutralizing antibody responses to reproductive hormones may be used for contraception. Neutralizing antibody response to hormones and other soluble factors that are required for the growth of particular tumors may also be considered as possible vaccination targets.

Analogous methods as described above for the use of anti-CTLA-4 antibody can be used for induction of therapeutic autoimmune responses, to treat patients having an inappropriate accumulation of other self-antigens, such as amyloid deposits, including Aβ in Alzheimer's disease, cytokines such as TNFα, and IgE.

EXAMPLES

The present invention is also described by means of the following examples. However, the use of these or other examples anywhere in the specification is illustrative only and in no way limits the scope and meaning of the invention or of any exemplified term. Likewise, the invention is not limited to any particular preferred embodiments described herein. Indeed, many modifications and variations of the invention may be apparent to those skilled in the art upon reading this specification and can be made without departing from its spirit and scope. The invention is therefore to be limited only by the terms of the appended claims along with the full scope of equivalents to which the claims are entitled.

Example 1

Anti-CTLA-4 Treatment Enhances Secondary Antibody and T Cell Responses to a Melanoma Cell Vaccine in Cynomolgus Monkeys The ability of a human anti-CTLA-4 antibody of the invention to enhance antibody and T cell responses to a melanoma cell vaccine was examined in cynomolgus monkeys (obtained from Primate Products, Miami, Fla.). Test groups of six monkeys each (three males, three females) were treated with either 1) a melanoma cell vaccine alone (SK-mel-3, a human melanoma tumor cell line transfected to express GM-CSF) or 2) both SK-mel-3 and the anti-CTLA-4 antibody 10D1 described in WO 01/14424. A whole cell vaccine would allow for investigation of autoimmune reactions to a variety of normal tissues in this animal model, despite the fact that the cellular vaccine was of human origin.

To prepare the vaccine, SK-mel cells were grown to confluency and harvested. The cells were treated with mitomycin C, washed several times and resuspended to $1 \times 10^7$/ml saline. The antibody was administered intravenously at a dosage of 10 mg/kg in a volume of 1.3 ml/kg. The SK-mel-3 cells were administered subcutaneously in a fixed amount ($5 \times 10^6$ cells/animal at 0.5 1111/animal). Each vaccine preparation was tested for endotoxin <2 ED/ml) and GM-CSF production after 48 hours (2-8 ng/ml per $10^6$ cells). The appropriate antibody 30 and/or vaccine were administered on days 0, 28, 56, 84 and 140. Antibody responses to the melanoma cell vaccine were assessed on days 13, 41, 69 and 97 using flow cytometry. The health status of the monkeys was assessed twice weekly and body weights were recorded weekly. Hematology, pharmacokinetic analysis and functional assays were performed prior to study initiation and periodically throughout the study. A complete macroscopic and microscopic pathology examination was performed at day 167.

The specificity of antibody responses in the animals treated with the melanoma vaccine and the anti-CTLA-4 antibody were examined. Plasma from 6 cynomolgus monkeys treated with the SK-mel-3 vaccine and the mAb 10D1 was obtained on day 41 of treatment and pooled. The plasma was diluted 1:1000 and tested for reactivity to a variety of melanoma and non-melanoma cell lines by flow cytometry. The results are shown in FIG. 1, which demonstrates that the antibody responses in the monkeys show greater specificity for human melanoma cell lines as compared to human non-melanoma cell lines or non-human cell lines.

Figure 2:
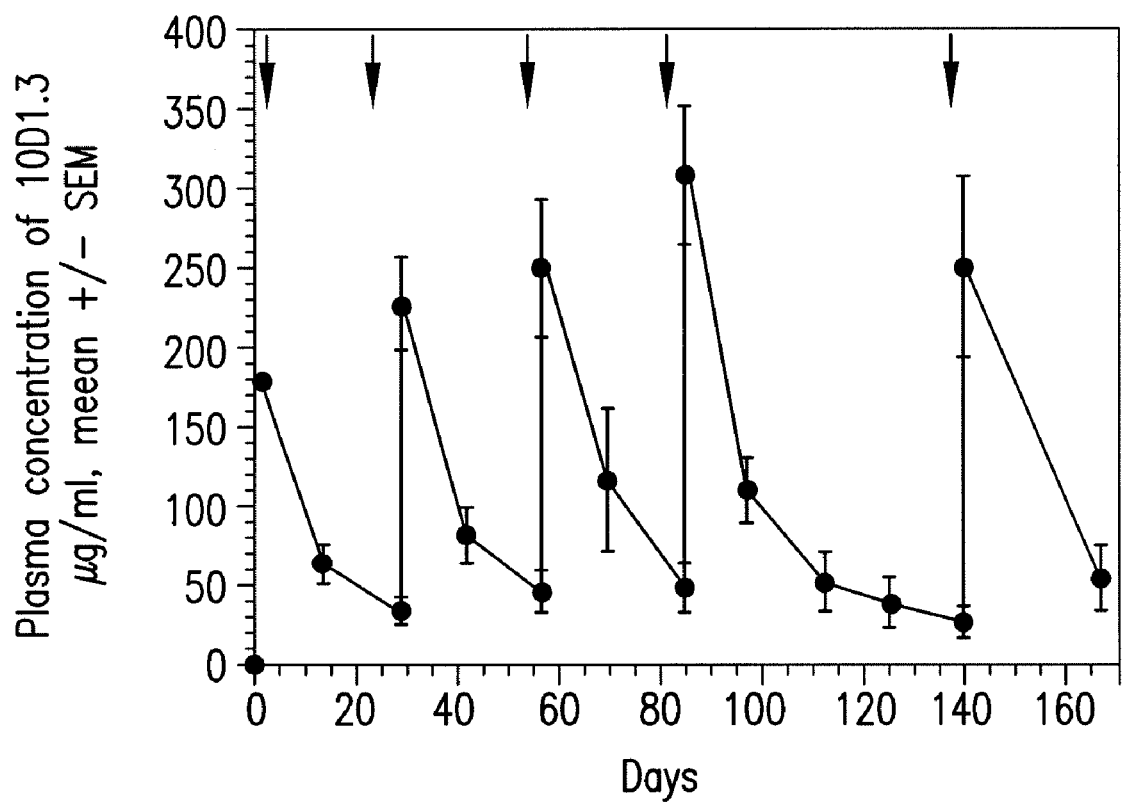
FIG. 2 shows the pharmacokinetic profile of the anti-CTLA-4 antibody 10D1 during chronic dosing of primates. Antibody was administered on days 0, 28, 56, 84 and 140 and plasma concentrations of 10D1 were analyzed by ELISA. The mean+/−SEM of six treated animals is shown.

The effect of chronic dosing on the monkeys treated with antibody and/or vaccine was assessed following administration of an additional dose at day 140. The plasma concentration of anti-CTLA-4 antibody was monitored by ELISA with recombinant CTLA-4 at various time points during the course of the study out to day 160. The 10D1 plasma concentrations were determined from dilutions of samples analyzed against a standard curve. The data for the plasma concentration of 10D1 during chronic dosing are shown in FIG. 2, where the mean+/−SEM of the six treated animals is presented. The results demonstrate the plasma levels of the anti-CTLA-4 antibody remained above detectable levels for the entire course of the 160 day period, suggesting that CTLA4 blockade was maintained throughout the treatment period. The mean plasma concentration for mAb 10D1 in the treated monkeys peaked between 175 and 315 µg/ml on the day post-infusion, and remained above 20 µg/ml during the six month study. Clinical chemistry, cage-side observations, and complete histology analysis did not reveal any significant alterations related to the antibody or vaccine administration. Chronic dosing did not result in treatment-related pathology except for slight irritation at the vaccine injection site of two monkeys, despite the potential ability of CTLA-4 blockade to establish autoreactive anti-melanocyte responses. The monkeys did not develop any detectable antibody response to 10D1 mAb and high levels of active circulating antibody were maintained for the duration of the study. Moreover, this chronic dosing with the anti-CTLA-4 antibody was associated with efficacy of treatment and was not associated with detrimental side effects (e.g., non-specific T cell activation). Thus, this experiment demonstrates that primates can be effectively treated for extended periods of time with an anti-CTLA-4 antibody such that plasma concentrations are maintained above detectable levels for at least 1, 2, 3, 4 or 5 months or even longer without serious side effects.

Example 2

Evidence of Antigen-Specific T Cell Proliferation from Delayed Type Hypersensitivity (DTH) Experiments in Humans Nineteen patients with resected Stage III (2 patients) or IV (17 patients) melanoma received escalating doses (0.3, 1 and 3 mg/kg) of CTLA-4 antibody 10D1 with each injection of gp100/tyrosinase/MART-1 peptide vaccine with incomplete Freund's adjuvant. The tyrosinase 368-376 (370D), MART-1 26-35 (27L) and gp100:209-217 (210M) peptides each differed from wild type by one amino acid modification to increase HLA binding. The vaccine was administered eight times over twelve months at 1 mg/dose/peptide. Immune responses measured by DTH reactivity indicated that four of nine patients responded to gp100 and two of nine patients responded to MART-I. ELISPOT assays showed immune responses in four of sixteen patients tested using fresh CD8 T cells.

Example 3

Results from Phase I Human Clinical Trials of MAb 10D1 Melanoma (MDXCTLA4-02)

MDXCTLA4-02 was a Phase I open-label, multicenter clinical trial to evaluate the safety and pharmacokinetics of MAb 10D1 in seventeen patients with progressive, unresectable, malignant melanoma. Median age was 59 years (range 29-79). Nine patients had received prior immunotherapy, six had prior radiation and five had prior chemotherapy. All patients received a single dose of 3 mg/kg of 10D1 intravenously over 90 minutes and were then followed for toxicity, pharmacokinetics, circulating T cell activation and clinical outcome. All infusions were completed with only mild adverse events. Seven patients had mild, reversible rashes or pruritis. Plasma levels of antibody persisted from one to four months. There was no significant increase in activated peripheral T cells and no evidence of clinical autoimmunity beyond the mild rash. Two patients experienced a partial response including resolution of three soft tissue masses and over 50% reduction of a lung mass. Furthermore, the patient experiencing the over 50% reduction in lung mass was a patient who previously had been treated with a melanoma vaccine, suggesting that the anti-CTLA-4 antibody treatment was capable of activating a pre-existing memory response to the tumor. The results of this study indicate that anti-CTLA-4 treatment was well tolerated with clear evidence of immunologic and anti-tumor activity.

Lymphocyte subpopulations in patients treated with 10D1 were analyzed by flow cytometry at various time points after antibody treatment. The results are summarized below in Table 1, below.

TABLE 1

Flow cytometric analysis of lymphocyte subpopulations in melanoma cancer subjects treated with 3.0 mg/Kg MAb 10D1.

| Sub-pop | Baseline | 24 Hours | Day 7 | Day 14 | Day 21 | Day 28 |
| --- | --- | --- | --- | --- | --- | --- |
| CD3 | 72.9 ± 3.6 | 68.9 ± 4.1 | 75.1 ± 3.6 | 73.2 ± 4.3 | 74.7 ± 3.9 | 74.2 ± 4.2 |
| CD4 | 48.8 ± 3.0 | 44.3 ± 3.6 | 49.3 ± 3.6 | 50.5 ± 3.8 | 49.2 ± 4.3 | 50.8 ± 4.5 |
| CD8 | 22.3 ± 2.5 | 25.3 ± 3.0 | 26.2 ± 2.5 | 21.9 ± 1.8 | 26.3 ± 2.9 | 23.7 ± 2.7 |
| CD19 | 12.2 ± 2.5 | 12.7 ± 3.0 | 8.7 ± 2.2 | 11.3 ± 2.9 | 9.4 ± 2.2 | 9.4 ± 2.1 |
| CD4 + CD25 | 65.8 ± 3.4 | 64.9 ± 4.0 | 60.8 ± 3.4 | 61.7 ± 3.0 | 58.3 ± 3.0 | 60.9 ± 2.9 |
| CD8 + CD25 | 14.4 ± 1.7 | 13.4 ± 1.8 | 13.1 ± 1.9 | 11.9 ± 1.6 | 10.9 ± 1.3 | 13.7 ± 2.1 |
| CD4 + HLA-DR | 11.8 ± 1.3 | 12.4 ± 1.7 | 19.7 ± 3.5 | 20.9 ± 1.9 | 18.4 ± 1.2 | 17.1 ± 1.6 |
| CD8 + HLA-DR | 13.6 ± 2.2 | 17.9 ± 2.8 | 17.7 ± 2.9 | 17.5 ± 2.3 | 20.2 ± 2.9 | 17.5 ± 2.6 |
| CD4 + 45RO | 23.7 ± 3.4 | 22.9 ± 3.7 | 19.4 ± 3.4 | 17.9 ± 3.8 | 17.3 ± 3.7 | 19.2 ± 3.8 |
| CD8 + 45RO | 40.5 ± 3.5 | 39.1 ± 3.8 | 37.6 ± 4.1 | 35.5 ± 4.9 | 35.1 ± 5.0 | 35.7 ± 4.3 |

Similar to the results observed in prostate cancer patients (see Example 6 below), the results in the melanoma study demonstrate that 10D1 treatment led to an approximately 50% increase in the CD4/HLA-DR+ subpopulation over time. The other lymphocyte subpopulations remained essentially constant over time. As described above, the ability of anti-CTLA4 antibody treatment to increase the CD4/HLA-DR+ subpopulation over time can be used as a selective feature when evaluating anti-CTLA4 antibodies (i.e., a panel of anti-CTLA4 antibodies can be evaluated for their ability to increase the CD4/HLA-DR+ subpopulation and an anti-CTLA4 antibody that is capable of increasing this subpopulation over time can be selected). Moreover, monitoring of lymphocyte subpopulations over time, in particular the CD4/HLA-DR+ subpopulation, can be performed in subjects being treated with anti-CTLA4 as one marker of the effectiveness of the antibody.

Example 4

Human Study of Anti-CTLA-4 Antibody Blockade in Previously Vaccinated Melanoma and Ovarian Cancer Patients Nine previously immunized advanced cancer patients were administered anti-CTLA-4 antibody 10D1. Patients 1-6 were enrolled through Phase I trial MDXCTLA4-02 with eligibility criteria of surgically unresectable stage III or IV melanoma, disease progression, a life expectancy of at least 12 weeks, adequate end organ function, stable analgesic therapy, and a Karnofsky performance status of at least 60%. Patients were excluded if they had a second malignancy (other than treated non-melanoma skin cancer or superficial bladder cancer), autoimmune disease, active infection, kanamycin hypersensitivity; or if they used corticosteroids. Patients 7-9 were enrolled through a Phase I trial for patients with metastatic melanoma, metastatic ovarian carcinoma, metastatic non-small cell lung carcinoma or acute myelogenous leukemia.

Four patients were previously treated for early stage melanoma (three patients received a-interferon, one patient received a vaccine of GM2 ganglioside admixed with QS-21, one patient received radiation). Prior non-immunologic treatments for metastatic melanoma included surgery (four patients), radiation (two patients), chemotherapy (three patients), and proteasome inhibitor (one patient). The two ovarian cancer patients received multiple chemotherapies for relapsing disease throughout the three to four years preceding the study.

All patients participated in Phase I vaccine studies for metastatic disease prior to entry into this study. Three melanoma and both ovarian cancer patients were immunized with irradiated, autologous tumor cells engineered to secrete GM-CSF by adenoviral mediated gene transfer. One of these patients (Patient 8) also received a MUC-1 vaccine. Three melanoma patients were immunized with autologous dendritic cells engineered to express gp100 and MART-1 by adenoviral mediated gene transfer. One melanoma patient was vaccinated with a modified gp100 peptide and high-dose interleukin-2.

Initially, 10D1 was administered intravenously as a test dose of 0.2 mg in 10 ml of normal saline over ten minutes to identify potential hypersensitivity reactions. The remainder of the 3 mg/kg 10D1 dose was then delivered intravenously over ninety minutes. Following antibody administration, patients underwent clinical, laboratory and radiographic evaluation daily for three days, then weekly for four weeks and then monthly.

One patient had an acute hypersensitivity reaction manifested by mild hypotension and nausea during the infusion. The reaction was easily managed with anti-histamines and the infusion was completed uneventfully. Five patients had transient Grade I/II constitutional symptoms including myalgia, arthralgia, anorexia, fatigue, nasal congestion, and cough for two to seven days following infusion. One patient had intermittently recurring symptoms for several months. One patient manifested a transient Grade III liver function abnormality.

The three melanoma patients previously vaccinated with irradiated, autologous GM-CSF secreting tumor cells had extensive tumor necrosis following treatment with 10D1.

Patient 1 had central nervous system, lung, abdomen and soft tissue metastases upon enrollment in the study. One month following 10D1 administration, Patient 1 exhibited clinical changes in his neurologic status and a subcutaneous lesion became acutely inflamed. Patient 1 died six days later. At autopsy, marked hemorrhagic tumor necrosis was noted of the brain, epidural and visceral metastases. Histopathologic examination showed extensive tumor destruction (at least 90%) with hemorrhage. Tumor blood vessels were severely damaged resulting in extensive ischemic necrosis. A rim of viable tumor cells remained in each lesion accompanied by a granulocyte and lymphocyte reaction.

Patient 2 had recurrent Grade II constitutional symptoms that began one month after 10D1 infusion. Biopsy of a mediastinal lesion showed extensive tumor necrosis with lymphocyte and granulocyte infiltrates. Immunohistochemistry showed the presence of $CD4^+$ and $CD8^+$ T cells and immunoglobulin-producing $CD20^+$ B lymphocytes. The mediastinal lesion was completely resected two months later. Pathologic analysis of the lesion showed dense fibrosis, extensive necrosis, and an ongoing lymphocyte and granulocyte response. A vasculopathy characterized by a circumferential lymphoid infiltrate in the wall of an occluded blood vessel was also noted. The tumor necrosis was spatially related to the vessel damage.

Patient 7 developed inflammation in a large subcutaneous lesion three weeks after 10D1 infusion. The lesion was excised two months after infusion. Pathologic examination of the lesion showed extensive tumor necrosis and fibrosis, a prominent vasculopathy, and lymphocyte and granulocyte infiltrates.

Less dramatic anti-tumor effects were noted in the four melanoma patients previously immunized with defined melanosomal antigens. Patient 3 underwent resection of an enlarging mediastinal lesion seven months after infusion. Pathologic analysis showed a dense lymphocytic infiltrate without tumor necrosis. Immunohistochemistry showed the presence of $CD8^+$ cells, but not $CD4^+$ or $CD20^+$ cells. Patient 4 had a similar $CD4^+$ cell infiltrate without tumor necrosis in a lymph node metastasis, which was excised two months after antibody infusion. Patient 5 did not have lymphoid infiltrates or tumor necrosis in a subcutaneous lesion, which was resected two months after antibody infusion. Patient 6 did not have a biopsy and his tumor progressed.

The antibody infusion resulted in changes in CA-125 levels in the two ovarian carcinoma patients. CA-125 is shed from the surface of ovarian carcinoma cells and is a useful marker of disease status. (Jacobs, I. (1994) Gyn. Oncol. 55:S22-27). Patient 8 had a 43% reduction in CA-125 values (230 to 132) that began two months after antibody infusion. This response was not maintained but a second infusion of 10D1 stabilized CA-125 levels for two 25 months. Patient 9 had a leveling off of CA-125 values one month following antibody infusion with a concomitant reduction in ascites. Patient 9 had a rapidly rising CA-125 prior to infusion.

Low titers of autoantibodies (anti-nuclear antibodies, anti-thyro globulin antibodies, rheumatoid factor) that persisted for 1-2 months were noted in four patients. There was no clinical evidence of autoimmune disease.

All melanoma patients developed an asymptomatic Grade I reticular and erythematous rash on the trunk and extremities between three days and three weeks after antibody infusion. Seven patients had a skin biopsy. Five of the seven patients biopsied had prominent peri-vascular T cells infiltrates in the superficial dermis that extended into the epidermis. $CD4^+$ and $CD8^+$ T cells were found apposed to dying melanocytes. Vitiligo was not clinically evident. Mild, focal hypo-pigmentation of the retina was noted in one patient, but visual acuity was not affected. One ovarian carcinoma patient developed an erythematous rash on the face and trunk two weeks after infusion. Skin biopsy showed peri-vascular T cell infiltrates in the superficial dermis but no reactivity towards melanocytes.

10D1 induced significant increases in circulating neutrophils, and neutrophil infiltrates were associated with tumor necrosis.

The results show that a single infusion of 10D1 anti-CTLA-4 antibody can have significant anti-tumor effects and can be safely administered to human patients. The generation of low titers of autoantibodies shows that the therapy may, at least partially, compromise systemic tolerance but no clinical evidence of autoimmune disease was noted.

Example 5

Study of Administration of Anti-CTLA-4 Antibody IODI in Conjunction with Peptide Vaccines to Patients with Melanoma Fourteen patients with progressive Stage 1V melanoma received anti-CTLA-4 antibody 10D1 in conjunction with vaccination with two HLA-A*0201-restricted gp100 peptides. Patient characteristics are summarized in Table 2, below.

TABLE 2

| Patient | Age/Sex | Disease Sites | Prior Therapy[1] | No. of treatment cycles[2] | Response[3] (months) | Grade I/II Toxicity | Grade III/IV Toxicity |
|---|---|---|---|---|---|---|---|
| 1 | 52/M | Lung | I, S | 2 | PR (10+) | | Enterocolitis, dermatitis |
| 2 | 40/F | Supraclavicular lymph node | C, I, S | 1 | NR | Vitiligo | Dermatitis |
| 3 | 39/M | Lung, Mediastinum, Subcutaneous | S | 6 | NR (mixed) | | |
| 4 | 55/F | Skin, Subcutaneous | I, S | 1 | NR | Pulmonary infiltrates | |
| 5 | 67/M | Liver, Retroperitoneum, subcutaneous | C, I, R, S | 4 | NR | ANA+[4] | |
| 6 | 59/M | Lung, Subcutaneous | I, S | 4 | NR | Vitiligo | |

TABLE 2-continued

| Patient | Age/Sex | Disease Sites | Prior Therapy[1] | No. of treatment cycles[2] | Response[3] (months) | Grade I/II Toxicity | Grade III/IV Toxicity |
|---|---|---|---|---|---|---|---|
| 7 | 48/M | Lung, Brain, Adrenal, Subcutaneous | C, I, S | 2 | NR | | |
| 8 | 48/M | Lung, Liver, Adrenal, Mesentery, Subcutaneous | C, I, S | 2 | NR | | |
| 9 | 53/M | Mediastinum, Mesentery, Skin | I, R, S | 2 | NR | | |
| 10 | 62/M | Lung, Hilum | C, I, S | 2 | NR (mixed) | | |
| 11 | 54/M | Lung, Brain, Subcutaneous | C, S | 5 | CR (7+) | | Hypophysitis |
| 12 | 43/M | Subdiaphragm, Muscle, Subcutaneous | I, S | 3 | NR | ANA+ | Hepatitis |
| 13 | 49/F | Lung, Subcutaneous | C, I, S | 4 | PR (6+) | | Dermatitis |
| 14 | 63/M | Lung, Pelvic lymph node | S | 4 | NR | | |

[1]C = chemotherapy, I = immunotherapy, R = radiotherapy, S = surgery.
[2]A treatment cycle consists of one infusion of CTLA-4 antibody and one vaccination with gp100: 209-217(210M) and gp100: 280-288(288V) peptides.
[3]NR = no response, PR = partial response, CR = complete response.
[4]ANA = anti-nuclear antibody.

All patients were HLA*0201+ with a Karnofsky performance status ≧60%. Six patients had visceral metastases. The patients had no evidence of autoimmune or immunodeficiency disease. All patients had prior surgery for their primary lesion. Six patients had prior chemotherapy. Eleven patients had prior immunotherapy including interferon-a (Patients 2, 5-8, 10, 12 and 13), low-dose IL-2 (Patients 2, 5 and 13), high-dose intravenous IL-2 (Patients 4, 7 and 8), whole cell melanoma vaccines (Patients 1, 2 and 6), NY-ESO-1 peptide vaccine (Patients 4 and 5), and GM-CSF (Patient 9). The patients had no prior gp100 immunization and had no systemic therapy in the three weeks prior to treatment.

A treatment cycle was administered every three weeks, which consisted of anti-CTLA-4 antibody 10D1 at 3 mg/kg administered intravenously over 90 minutes followed by 1 mg of gp100:209-217(210M) peptide (IMDQVPFSV; SEQ ID NO:1) emulsified in incomplete Freund's adjuvant (IFA) injected subcutaneously in one extremity and 1 mg of gp100: 280-288(288V) peptide (YLEPGPVTV; SEQ ID NO:2) emulsified in IFA injected subcutaneously in a second extremity (synthetic peptides provided by the National Cancer Institute Cancer Therapy Evaluation Program). Patients underwent apheresis prior to treatment and three weeks following every two treatment cycles. Peripheral blood mononuclear cells (PBMC) were isolated by Ficoll-Hypaque separation and cryopreserved in heat-inactivated human AB serum with 10% dimethyl sulphoxide and stored at −180° C. until further use. Patients received from 1 to 6 treatment cycles (Table 2).

Clinical response was evaluated using computed axial tomography (CT) of the chest, abdomen and pelvis; and magnetic resonance imaging (MRI) of the brain. These imaging studies were performed within 4 weeks of starting treatment and then after every two treatment cycles. Additional radiological studies were used as needed to evaluate disease sites. The sum of the longest diameters of the tumors in each patient (World Health Organization RECIST criteria) was calculated before and after treatment. A partial response was defined as a decrease of at least 30%, but less than 100%, in the sum of the longest diameters of all evaluable metastases lasting at least one month, and no new or enlarging tumors. A complete response was defined as a decrease of 100% in the sum of the longest diameters of all evaluable metastases lasting at least one month, and no new tumors. A non-response was defined as response that was not a partial or a complete response.

Patients were evaluated for autoimmune responses. Patients received an ophthalmologic examination prior to treatment and three months following initiation treatment. All patients had negative serum blood tests prior to initiation of the study for thyroglobulin Ab, rheumatoid factor and anti-nuclear antibody. Human anti-human (anti-idiotypic) Ab, erythrocyte sedimentation rate, anti-nuclear Ab, thyroid stimulating hormone and free T4 levels were measured every three weeks during the study.

Plasma concentrations of 10D1 were determined using standard ELISA with microtiter wells coated with CTLA-4-Ig (R&D Systems, Minneapolis, Minn.). Dilutions of plasma samples were incubated on the plates. Bound anti-CTLA-4 Ab was detected with alkaline phosphatase-labeled goat anti-human IgG F(ab)-specific probe, which was developed with p-NPP substrate.

A twelve-day in vitro sensitization assay, which is more sensitive than ELISPOT or tetramer assays, was used to assess immunologic reactivity in all eleven patients with PBMC available for testing. (Rosenberg, S. A. et al., Nat. Med. 1998; 4:321-327). Cryopreserved PBMC were thawed and cultured in complete Iscove's-based media with 10% heat-inactivated human AB serum with 1 μM of native gp100: 209-217 or gp100:280-288 peptide and 300 IU/ml IL-2. Cells were harvested 11 to 13 days after initiation of the culture and co-incubated with tumor cells or peptide-pulsed T2 cells overnight. Interferon-γ, (IFN-γ) release in the supernatant was measured using commercial ELISA assays (Pierce-Endogen, Rockford, Ill.). All eleven patients exhibited successful immunization against the native gp 100:209-217 peptide after one to four treatment cycles. Six patients were successfully immunized against the native gp100:280288 peptide.

Flow cytometry analyses were performed after Fc-receptor blocking and staining with antibodies (BD Biosciences, San Diego, Calif.) or tetramers (Beckman Coulter Immunomics, San Diego, Calif.). Surface marker expression on PBMC of nine patients before and after two cycles of treatment was compared. HLA-DR (an activation marker) expression was significantly increased on post-therapy CD3$^+$ CD4$^+$ cells (P=0.0004; paired t-test) and CD3$^+$CD4$^+$ (presumably CD8$^+$) cells (P=0.04). CD3$^+$CD4$^+$ cells also showed significantly increased expression of CD45RO (a memory cell marker) post-therapy (P=0.04). The percent of cell populations expressing CD69, CD25 and CTLA-4 did not change.

Patients 1, 11 and 13 were responders. (Table 15) Patient 1 had shrinkage of a solitary lung lesion after two treatment cycles. Patient 13 had shrinkage of a solitary lung lesion and complete resolution of a subcutaneous lesion after two treatment cycles. Patient 11 had 31 lung lesions, two subcutaneous lesions and one brain lesion. The brain lesion grew from 0.5 cm to approximately 1.0 cm after two treatment cycles. Following three additional treatment cycles, Patient 11 had complete resolution of all lesions, including the brain lesion.

Patient 3 had a mixed response in which several lung lesions resolved after four treatment cycles but mediastinal lymph nodes enlarged. Patient 10 had significant shrinkage of a hilar lesion and several other lung lesions after two treatment cycles, but other lung lesions enlarged.

Grade I/II adverse events included diarrhea (Patients 3, 5 and 14), skin rash (Patient 14), pulmonary infiltrates and mild pleuritic chest pain (Patient 4) and vitiligo (Patients 2 and 6).

Six patients developed seven Grade III/IV adverse events including dermatitis (Patients 1, 2 and 13), colitis/enterocolitis (Patients 1 and 9), hypophysitis (inflammation of the pituitary gland) (Patient 11), and hepatitis (Patient 12). All patients recovered following discontinuation of treatment and the administration of supportive care and/or steroid therapy. There were no relapses or subsequent autoimmune events.

Autoimmune screening blood tests were normal except for Patients 5 and 12 who developed anti-nuclear Ab.

This study demonstrated objective evidence of metastatic melanoma tumor regression in patients receiving anti-CTLA-4 antibody 10D1 in conjunction with two peptide vaccines.

Example 6

A Phase I Human Clinical Trial of MAb tODt in Prostate Cancer (MDXCTLA4-01)

MDXCTLA4-01 was an open-label study of anti-cytotoxic T-lymphocyte-associated antigen-4 (anti-CTLA-4) monoclonal antibody 10D1 (MAb10D1) in patients with progressive, metastatic, hormone-refractory prostate cancer. Treatment was a single dose of MAb 10D1 that was administered intravenously, as an infusion, at a dosage of 3.0 mg/kg.

Patients with histologic diagnosis of primary adenocarcinoma of the prostate, and progressive metastatic carcinoma of the prostate after androgen deprivation and at least one systemic non-hormonal manipulation, were screened for participation in this study. Enrollment criteria were: progressive measurable disease, progressive PSA, PSA >5 ng/ml, testosterone <50 ng/dl, primary gonadal androgen suppression, life expectancy >12 weeks, and Karnofsky Performance Status >60%.

Because of the importance of monitoring the immune status of patients in the trial and the specific goal of monitoring generalized effects on T cell activation by anti-CTLA-4 antibody, the entry criteria in this study included minimum levels of CD4 and CD8 T cells of $\geq$500/ml and $\geq$500/ml respectively. However, it was observed during the initial accrual in the study that prostate cancer patients have significantly reduced T cell numbers although CD4 and CD8 T cells are clearly present. Many patients were initially rejected based on the above entry criteria. The apparent reduced T cell counts observed is a previously undocumented observation in prostate cancer patients that may have relevance in treatments involving cancer vaccination in these patients. Subsequent to these observations, the entry criteria were amended to include patients having CD4 and CD8 count of 300/ml and ~200/ml respectively.

Subjects underwent physical examination, ECG, chest radiography, diagnostic imaging, and blood sampling for hematological, biochemical, and immune function assessments. Monthly telephone interviews were used until six months after treatment to collect and record information on a subset of adverse events, including autoimmune adverse events after disease progression. PSA (decline, duration of decline, progression, time to progression) and disease response (complete, partial, stable, progressive) were monitored. Plasma concentrations of MAb 10D1 were being assessed immediately prior to, during, and up to two months after, infusion.

Figure 3:
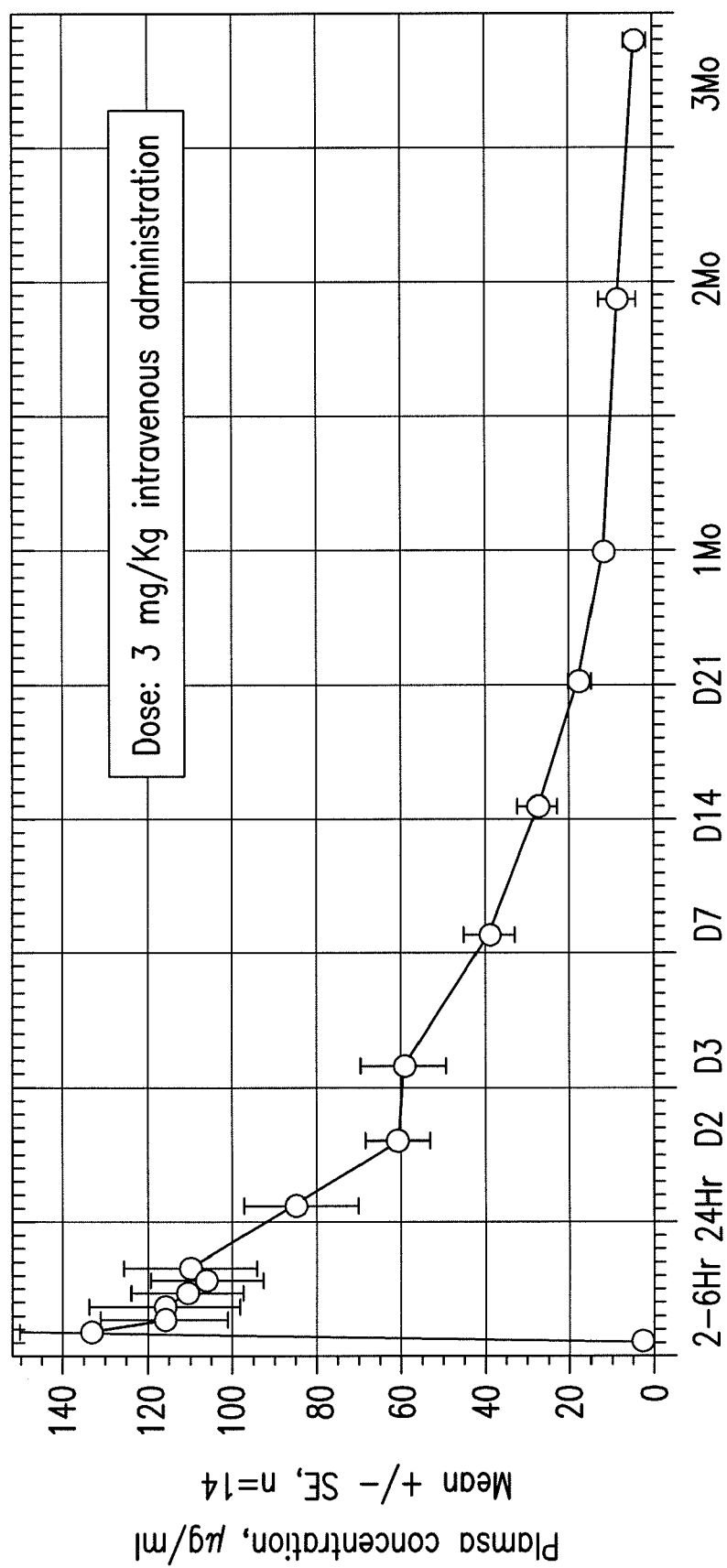
FIG. 3 shows the pharmacokinetic profile of anti-CTLA-4 antibody 10D1 in prostate cancer patients treated with a single dose of 10D1 at day 0. Plasma concentration (μg/ml) is shown. The mean+/−SEM for 14 treated patients is shown.

Fourteen patients with HRPC were enrolled. Median age was 69 years (range 56-79). Seven patients had received prior chemotherapy. All patients received a single dose of 3 mg/kg 10D1 intravenously over 90 minutes and were then followed for toxicity, pharmacokinetics, circulating T cell activation and clinical outcome. All infusions were completed as planned with only mild infusion related adverse events (AE). Mild and reversible rashes or pruritis responded to oral steroid therapy. No other AE of grade 3 or greater was 30 related to 10D1. The pharmacokinetic profile is shown in FIG. 3, which presents plasma concentration in μg/ml. The mean+/-SEM is shown for the 14 patients (n=14). The results shown in FIG. 3 demonstrate that plasma levels of the antibody were detectable for up to 3 months and additional monitoring has found that plasma levels can be detectable for even 4 months. There was no significant increase in activated peripheral T cells, and no clinical autoimmunity was noted. Two of 7 patients who were chemotherapy naive had a PSA response (consensus criteria) lasting 3 and 5 months, one with symptomatic improvement. Other patients experienced significant change in the slope of the curve for PSA. Patients were retreated with a second dose of 10D1 (3 mg/kg) and upon retreatment, patients who had previously responded again experienced PSA reductions without significant AE. The treatment was well tolerated with clear evidence of immunologic and anti-tumor activity. Thus, this studies demonstrate that human patients can be treated with an anti-CTLA-4 antibody such that plasma levels of the antibody remain above detectable levels for 1, 2, 3 or even 4 months without detrimental side effects.

Lymphocyte subpopulations in patients treated with 10D1 were analyzed by flow cytometry at various time points after antibody treatment. The results are summarized below in Table 3 (data is presented as mean+/-SEM).

TABLE 3

Flow cytometric analysis of lymphocyte subpopulations in prostate cancer subjects treated with 3.0 mg/Kg MAb 10D1.

| Sub-pop | Baseline | 24 Hours | Day 7 | Day 14 | Day 21 | Day 28 |
|---|---|---|---|---|---|---|
| CD3 | 71.7 ± 3.45 | 75.6 ± 3.53 | 77.6 ± 2.45 | 78.5 ± 2.49 | 75.6 ± 2.42 | 76.0 ± 2.70 |
| CD4 | 40.3 ± 3.49 | 38.7 ± 3.36 | 44.0 ± 3.20 | 38.7 ± 3.36 | 42.9 ± 2.98 | 44.5 ± 3.05 |
| CD8 | 30.5 ± 3.91 | 35.6 ± 4.54 | 32.6 ± 4.43 | 30.8 ± 4.14 | 31.5 ± 4.28 | 30.7 ± 4.32 |
| CD19 | 7.6 ± 1.24 | 5.7 ± 1.27 | 6.4 ± 1.24 | 6.2 ± 0.98 | 6.7 ± 1.27 | 6.8 ± 1.15 |
| CD4 + CD25 | 69.2 ± 3.47 | 65.0 ± 3.38 | 66.0 ± 3.28 | 63.7 ± 3.09 | 65.6 ± 2.97 | 64.5 ± 3.25 |
| CD8 + CD25 | 14.0 ± 2.54 | 11.2 ± 1.56 | 13.8 ± 2.91 | 15.4 ± 2.56 | 14.3 ± 2.68 | 15.5 ± 2.92 |
| CD4 + HLA-DR | 11.3 ± 2.78 | 11.4 ± 3.12 | 14.2 ± 2.49 | 17.1 ± 3.33 | 17.3 ± 3.32 | 17.4 ± 3.81 |
| CD8 + HLA-DR | 20.4 ± 3.44 | 21.5 ± 3.64 | 19.8 ± 3.87 | 20.6 ± 4.28 | 21.8 ± 3.82 | 20.7 ± 4.66 |
| CD4 + 45RO | 68.0 ± 4.98 | 72.4 ± 4.37 | 76.1 ± 4.19 | 76.0 ± 3.58 | 76.8 ± 3.93 | 76.9 ± 4.10 |
| CD8 + 45RO | 41.9 ± 6.00 | 44.8 ± 5.83 | 48.7 ± 6.04 | 48.4 ± 5.20 | 50.7 ± 5.64 | 50.7 ± 5.43 |

The results demonstrate that 10D1 treatment led to an approximately 50% increase in the CD4/HLA-DR+ subpopulation over time. The other lymphocyte subpopulations remained essentially constant over time.

In order to evaluate whether administration of MAb 10D1 can induce undesirable non-specific T cell activation, peripheral blood lymphocytes from the prostate cancer subjects were analyzed by flow cytometry for each of the following markers: CD4, CD8, CD25, CD44, CD69 and HLA-DR. No significant change in the frequency of any of these markers was observed during the course of the treatment for each of the prostate cancer subjects treated thus far. An example of this analysis is shown in Table 4 which shows the frequency of CD4, CD25, CD69-positive cells and CDS, CD25, CD69-positive cells at times prior to, during, and subsequent to MAb 10D1 administration in two of the subjects. These data demonstrate that MAb laD1 does not result in non-specific T cell activation.

Table 4. Flow cytometric analysis of T cell activation markers in prostate cancer subjects treated with 3.0 mg/Kg MAb 10D1.

TABLE 4

Flow cytometric analysis of T cell activation markets in prostate cancer subjects treated with 3.0 mg/Kg MAb 10D1.

| Patient Number | Time Point | CD(4 + 25 + 69) % | CD (8 + 25 + 69) % |
|---|---|---|---|
| 3 | Screen | 1.7 | 0.8 |
| 3 | −30 MIN (Pre-Infusion) | 2.6 | 0.8 |
| 3 | 40 MIN | 2.5 | 0.7 |
| 3 | 130 MIN | 1.9 | 0.9 |
| 3 | 145 MIN | 1.7 | 0.5 |
| 3 | 160 MIN | 1.7 | 1 |
| 3 | 190 MIN | 1.5 | 1.5 |
| 3 | 250 MIN | 2.1 | 1.2 |
| 3 | 370 MIN | 1.3 | 0.9 |
| 3 | 24 HR | 1.6 | 1.6 |
| 3 | 48 HR | 2.7 | 3 |
| 3 | 72 HR | 0.9 | 0.5 |
| 3 | Day 7 | 0.9 | 0.1 |
| 3 | Day 14 | 0.4 | 0.5 |
| 3 | Day 21 | 2.3 | 1.9 |
| 4 | Screen | 1.4 | 0.8 |
| 4 | −30 MIN (Pre-Infusion) | 0.5 | 0.3 |
| 4 | 40 MIN | 0.3 | 0.1 |
| 4 | 130 MIN | 0.3 | 0.1 |
| 4 | 145 MIN | 0.4 | 0.2 |
| 4 | 160 MIN | 0.2 | 0.2 |
| 4 | 190 MIN | 0.8 | 0.3 |
| 4 | 250 MIN | 0.1 | 0 |
| 4 | 370 MIN | 0.3 | 0.1 |
| 4 | 24 HR | 0.2 | 0.3 |
| 4 | 48 HR | 0.4 | 0.6 |
| 4 | Day 7 | 0.8 | 0.3 |
| 4 | Day 14 | 1 | 0.7 |
| 4 | Day 21 | 1.1 | 0.8 |

Figure 4:
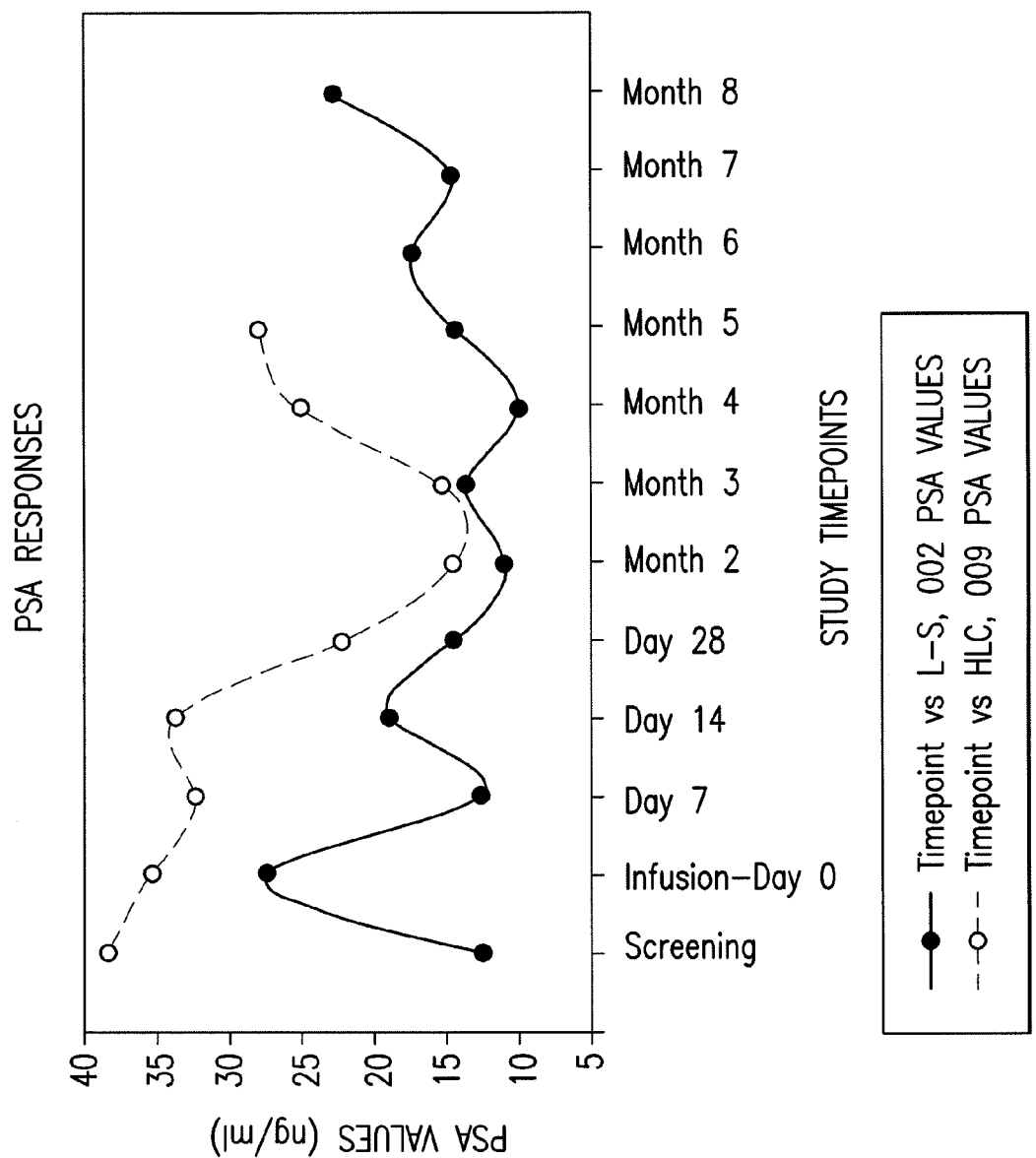
FIG. 4 shows prostate specific antigen (PSA) levels in ng/ml in two human patients at various time points after infusion of an anti-CTLA4 antibody at day 0.

Results from the MDXCTLA4-01 clinical trial have demonstrated that the infusions are tolerable with only minor reactions. Prolonged plasma half-life of the antibody was seen, with the antibody remaining in the plasma for approximately 3 to 4 months. Clear evidence of immune effects was observed without significant non-specific T cell activation. Symptomatic relief and reductions in prostate specific antigen (PSA) levels have been observed in prostate cancer patients treated with the anti-CTLA-4 antibody. Representative results for reductions in PSA levels are shown in FIG. 4, which shows PSA levels (in ng/ml) in two patients (one represented by the closed circles, the other by the open circles) at various time points after infusion of 3 mg/kg anti-CTLA-4 antibody at day 0. The results demonstrate that PSA levels decreased after infusion of the antibody and remained suppressed for approximately 3-4 months after treatment, correlating with the presence of the anti-CTLA-4 antibody in the plasma. Some other minor immune effects were also observed including immune-mediated rash and pruritis, transient seroconversion to positive autoantibodies, melanin pigment changes in melanoma patients and inflammatory reactions at tumor sites. Except for the rash and pruritis, all potentially adverse immune effects were subclinical. In summary, the ongoing results from human clinical trials with anti-CTLA-4 antibody treatment demonstrate that the antibody is well-tolerated and stimulates immune effects in recipients.

REFERENCES CITED

Numerous references, including patents, patent applications and various publications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entirety and to the same extent as if each reference was individually incorporated by reference.

What is claimed is:

1. A method for inducing or enhancing a memory immune response to an antigen in a human patient, which comprises administering to the patient who has developed a primary immune response to the antigen an anti-CTLA-4 antibody such that plasma concentration of the anti-CTLA-4 antibody is maintained above detectable levels for greater than four months, wherein the anti-CTLA-4 antibody comprises a heavy chain variable region that comprises CDR1, CDR2, and CDR3 domains; and a light chain variable region that comprises CDR1, CDR2, and CDR3 domains, wherein the heavy chain variable region CDR1 comprises amino acids having the sequence set forth in SEQ ID NO:3; the heavy chain variable region CDR2 comprises amino acids having the sequence set forth in SEQ ID NO:4; the heavy chain variable region CDR3 comprises amino acids having the sequence set forth in SEQ ID NO:5; the light chain variable region CDR1 comprises amino acids having the sequence set forth in SEQ ID NO:6; the light chain variable region CDR2 comprises amino acids having the sequence set forth in SEQ ID NO:7; and the light chain variable region CDR3 comprises amino acids having the sequence set forth in SEQ ID NO:8.

2. The method of claim 1, wherein the anti-CTLA-4 antibody is administered multiple times.

3. The method of claim 1, wherein the anti-CTLA-4 antibody is administered in an amount and at intervals such that the plasma concentration of anti-CTLA-4 antibody in the patient is at least 2 µg/ml for greater than four months.

4. The method of claim 1, wherein the anti-CTLA-4 antibody is administered in an amount and at intervals such that the plasma concentration of anti-CTLA-4 antibody in the patient is at least 5 µg/ml for greater than four months.

5. The method of claim 1, wherein the anti-CTLA-4 antibody is administered in an amount and at intervals such that the plasma concentration of anti-CTLA-4 antibody in the patient is at least 10 µg/ml for greater than four months.

6. The method of claim 1, wherein the antigen is a cancer antigen and the patient has been previously treated with surgery to resect a tumor.

7. The method of claim 1, wherein the antigen is a cancer antigen and the patient has been previously treated with chemotherapy.

8. The method of claim 1, wherein the antigen is a cancer antigen and the patient has been previously treated with radiation.

9. The method of claim 6, wherein the cancer antigen is a melanoma antigen.

10. The method of claim 7, wherein the cancer antigen is a melanoma antigen.

11. The method of claim 8, wherein the cancer antigen is a melanoma antigen.

12. The method of claim 1, wherein the patient is immunocompromised.

13. The method of claim 1, wherein the anti-CTLA-4 antibody is administered in a single dose.

14. The method of claim 1, wherein administration of the anti-CTLA-4 antibody does not result in detrimental side-effects.

15. A method for inducing or enhancing a memory immune response to an antigen in a human patient, which comprises administering to the patient an anti-CTLA-4 antibody such that plasma concentration of the anti-CTLA-4 antibody is maintained above detectable levels for greater than four months, wherein the anti-CTLA-4 antibody comprises a heavy chain variable region that comprises CDR1, CDR2, and CDR3 domains; and a light chain variable region that comprises CDR1, CDR2, and CDR3 domains, wherein the heavy chain variable region CDR1 comprises amino acids having the sequence set forth in SEQ ID NO:3; the heavy chain variable region CDR2 comprises amino acids having the sequence set forth in SEQ ID NO:4; the heavy chain variable region CDR3 comprises amino acids having the sequence set forth in SEQ ID NO:5; the light chain variable region CDR1 comprises amino acids having the sequence set forth in SEQ ID NO:6; the light chain variable region CDR2 comprises amino acids having the sequence set forth in SEQ ID NO:7; and the light chain variable region CDR3 comprises amino acids having the sequence set forth in SEQ ID NO:8.

16. The method of claim 15, wherein the anti-CTLA-4 antibody is administered multiple times.

17. The method of claim 15, wherein the anti-CTLA-4 antibody is administered in an amount and at intervals such that the plasma concentration of anti-CTLA-4 antibody in the patient is at least 2 µg/ml for greater than four months.

18. The method of claim 15, wherein the anti-CTLA-4 antibody is administered in an amount and at intervals such that the plasma concentration of anti-CTLA-4 antibody in the patient is at least 5 µg/ml for greater than four months.

19. The method of claim 15, wherein the anti-CTLA-4 antibody is administered in an amount and at intervals such that the plasma concentration of anti-CTLA-4 antibody in the patient is at least 10 µg/ml for greater than four months.

20. The method of claim 15, wherein the antigen is a cancer antigen and the patient has been previously treated with surgery to resect a tumor.

21. The method of claim 15, wherein the antigen is a cancer antigen and the patient has been previously treated with chemotherapy.

22. The method of claim 15, wherein the antigen is a cancer antigen and the patient has been previously treated with radiation.

23. The method of claim 20, wherein the cancer antigen is a melanoma antigen.

24. The method of claim 21, wherein the cancer antigen is a melanoma antigen.

25. The method of claim 22, wherein the cancer antigen is a melanoma antigen.

26. The method of claim 15, wherein the patient is immunocompromised.

27. The method of claim 15, wherein the anti-CTLA-4 antibody is administered in a single dose.

28. The method of claim 15, wherein administration of the anti-CTLA-4 antibody does not result in detrimental side-effects.

29. A method for treating cancer in a human patient, which comprises administering to the patient an anti-CTLA-4 antibody such that plasma concentration of the anti-CTLA-4 antibody is maintained above detectable levels for greater than four months, wherein the anti-CTLA-4 antibody comprises a heavy chain variable region that comprises CDR1, CDR2, and CDR3 domains; and a light chain variable region that comprises CDR1, CDR2, and CDR3 domains, wherein the heavy chain variable region CDR1 comprises amino acids having the sequence set forth in SEQ ID NO:3; the heavy chain variable region CDR2 comprises amino acids having the sequence set forth in SEQ ID NO:4; the heavy chain variable region CDR3 comprises amino acids having the sequence set forth in SEQ ID NO:5; the light chain variable region CDR1 comprises amino acids having the sequence set forth in SEQ ID NO:6; the light chain variable region CDR2 comprises amino acids having the sequence set forth in SEQ ID NO:7; and the light chain variable region CDR3 comprises amino acids having the sequence set forth in SEQ ID NO:8.

30. The method of claim 29, wherein the anti-CTLA-4 antibody is administered multiple times.

31. The method of claim 29, wherein the anti-CTLA-4 antibody is administered in an amount and at intervals such that the plasma concentration of anti-CTLA-4 antibody in the patient is at least 2 µg/ml for greater than four months.

32. The method of claim 29, wherein the anti-CTLA-4 antibody is administered in an amount and at intervals such that the plasma concentration of anti-CTLA-4 antibody in the patient is at least 5 µg/ml for greater than four months.

33. The method of claim 29, wherein the anti-CTLA-4 antibody is administered in an amount and at intervals such that the plasma concentration of anti-CTLA-4 antibody in the patient is at least 10 µg/ml for greater than four months.

34. The method of claim 29, wherein the patient is immunocompromised.

35. The method of claim 29, wherein the anti-CTLA-4 antibody is administered in a single dose.

36. The method of claim 29, wherein administration of the anti-CTLA-4 antibody does not result in detrimental side-effects.

37. The method of claim 29, wherein the cancer is melanoma.

38. The method of claim 29, wherein the patient has been previously treated with surgery to resect a tumor.

39. The method of claim 29, wherein the patient has been previously treated with chemotherapy.

40. The method of claim 29, wherein the patient has been previously treated with radiation.

41. The method of claim 1, wherein the anti-CTLA-4 antibody comprises a heavy chain variable region comprising amino acids comprising the sequence set forth in SEQ ID NO:9; and a light chain variable region comprising amino acids comprising the sequence set forth in SEQ ID NO:10.

42. The method of claim 15, wherein the anti-CTLA-4 antibody comprises a heavy chain variable region comprising amino acids comprising the sequence set forth in SEQ ID NO:9; and a light chain variable region comprising amino acids comprising the sequence set forth in SEQ ID NO:10.

43. The method of claim 29, wherein the anti-CTLA-4 antibody comprises a heavy chain variable region comprising amino acids comprising the sequence set forth in SEQ ID NO:9; and a light chain variable region comprising amino acids comprising the sequence set forth in SEQ ID NO:10.

44. A method for inducing or enhancing a memory immune response to an antigen in a human patient, which comprises administering to the patient who has developed a primary immune response to the antigen an anti-CTLA-4 antibody such that plasma concentration of the anti-CTLA-4 antibody is maintained above detectable levels for greater than four months, wherein the anti-CTLA-4 antibody comprises a heavy chain variable region that comprises CDR1, CDR2, and CDR3 domains; and a light chain variable region that comprises CDR1, CDR2, and CDR3 domains, wherein the heavy chain variable region CDR3 comprises amino acids having the sequence set forth in SEQ ID NO:5 and the light chain variable region CDR3 comprises amino acids having the sequence set forth in SEQ ID NO:8.

45. The method of claim 44, wherein the heavy chain variable region CDR2 of the anti-CTLA-4 antibody comprises amino acids having the sequence set forth in SEQ ID NO:4 and the light chain variable region CDR2 of the anti-CTLA-4 antibody comprises amino acids having the sequence set forth in SEQ ID NO:7.

46. The method of claim 44 or 45, wherein the heavy chain variable region CDR1 of the anti-CTLA-4 antibody comprises amino acids having the sequence set forth in SEQ ID NO:3 and the light chain variable region CDR1 of the anti-CTLA-4 antibody comprises amino acids having the sequence set forth in SEQ ID NO:6.

47. A method for treating cancer in a human patient, which comprises administering to the patient an anti-CTLA-4 antibody such that plasma concentration of the anti-CTLA-4 antibody is maintained above detectable levels for greater than four months, wherein the anti-CTLA-4 antibody comprises a heavy chain variable region that comprises CDR1, CDR2, and CDR3 domains; and a light chain variable region that comprises CDR1, CDR2, and CDR3 domains, wherein the heavy chain variable region CDR3 comprises amino acids having the sequence set forth in SEQ ID NO:5 and the light chain variable region CDR3 comprises amino acids having the sequence set forth in SEQ ID NO:8.

48. The method of claim 47, wherein the heavy chain variable region CDR2 of the anti-CTLA-4 antibody comprises amino acids having the sequence set forth in SEQ ID NO:4 and the light chain variable region CDR2 of the anti-CTLA-4 antibody comprises amino acids having the sequence set forth in SEQ ID NO:7.

49. The method of claim 47 or 48, wherein the heavy chain variable region CDR1 of the anti-CTLA-4 antibody comprises amino acids having the sequence set forth in SEQ ID NO:3 and the light chain variable region CDR1 of the anti-CTLA-4 antibody comprises amino acids having the sequence set forth in SEQ ID NO:6.

50. The method of claim 44, wherein the anti-CTLA-4 antibody comprises a heavy chain variable region comprising amino acids comprising the sequence set forth in SEQ ID NO:9; and a light chain variable region comprising amino acids comprising the sequence set forth in SEQ ID NO:10.

51. The method of claim 47, wherein the anti-CTLA-4 antibody comprises a heavy chain variable region comprising amino acids comprising the sequence set forth in SEQ ID NO:9; and a light chain variable region comprising amino acids comprising the sequence set forth in SEQ ID NO:10.

52. The method of claim 44, wherein the anti-CTLA-4 antibody is administered multiple times.

53. The method of claim 44, wherein the anti-CTLA-4 antibody is administered in an amount and at intervals such that the plasma concentration of the anti-CTLA-4 antibody in the patient is at least 2 μg/ml for greater than four months.

54. The method of claim 44, wherein the anti-CTLA-4 antibody is administered in an amount and at intervals such that the plasma concentration of anti-CTLA-4 antibody in the patient is at least 5 μg/ml for greater than four months.

55. The method of claim 44, wherein the anti-CTLA-4 antibody is administered in an amount and at intervals such that the plasma concentration of anti-CTLA-4 antibody in the patient is at least 10 μg/ml for greater than four months.

56. The method of claim 44, wherein the antigen is a cancer antigen and the patient has been previously treated with surgery to resect a tumor.

57. The method of claim 44, wherein the antigen is a cancer antigen and the patient has been previously treated with chemotherapy.

58. The method of claim 44, wherein the antigen is a cancer antigen and the patient has been previously treated with radiation.

59. The method of claim 56, wherein the cancer antigen is a melanoma antigen.

60. The method of claim 57, wherein the cancer antigen is a melanoma antigen.

61. The method of claim 58, wherein the cancer antigen is a melanoma antigen.

62. The method of claim 54, wherein the patient is immunocompromised.

63. The method of claim 44, wherein the anti-CTLA-4 antibody is administered in a single dose.

64. The method of claim 44, wherein administration of the anti-CTLA-4 antibody does not result in detrimental side-effects.

65. The method of claim 47, wherein the anti-CTLA-4 antibody is administered multiple times.

66. The method of claim 47, wherein the anti-CTLA-4 antibody is administered in an amount and at intervals such that the plasma concentration of anti-CTLA-4 antibody in the patient is at least 2 μg/ml for greater than four months.

67. The method of claim 47, wherein the anti-CTLA-4 antibody is administered in an amount and at intervals such that the plasma concentration of anti-CTLA-4 antibody in the patient is at least 5 μg/ml for greater than four months.

68. The method of claim 47, wherein the anti-CTLA-4 antibody is administered in an amount and at intervals such that the plasma concentration of anti-CTLA-4 antibody in the patient is at least 10 μg/ml for greater than four months.

69. The method of claim 47, wherein the patient is immunocompromised.

70. The method of claim 47, wherein the anti-CTLA-4 antibody is administered in a single dose.

71. The method of claim 47, wherein administration of the anti-CTLA-4 antibody does not result in detrimental side-effects.

72. The method of claim 47, wherein the cancer is melanoma.

73. The method of claim 47, wherein the patient has been previously treated with surgery to resect a tumor.

74. The method of claim 47, wherein the patient has been previously treated with chemotherapy.

75. The method of claim 47, wherein the patient has been previously treated with radiation.

* * * * *

SEQUENCE LISTING

```
<160> NUMBER OF SEQ ID NOS: 10

<210> SEQ ID NO 1
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 1

Ile Met Asp Gln Val Pro Phe Ser Val
 1               5

<210> SEQ ID NO 2
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 2

Tyr Leu Glu Pro Gly Pro Val Thr Val
 1               5

<210> SEQ ID NO 3
<211> LENGTH: 5
<212> TYPE: PRT
<213> ORGANISM: Homo sapiens
<220> FEATURE:
<223> OTHER INFORMATION: heavy chain CDR1 for 10D1

<400> SEQUENCE: 3

Ser Tyr Thr Met His
 1               5

<210> SEQ ID NO 4
<211> LENGTH: 17
<212> TYPE: PRT
<213> ORGANISM: Homo sapiens
<220> FEATURE:
<223> OTHER INFORMATION: heavy chain CDR2 for 10D1

<400> SEQUENCE: 4

Phe Ile Ser Tyr Asp Gly Asn Asn Lys Tyr Tyr Ala Asp Ser Val Lys
 1               5                  10                  15

Gly

<210> SEQ ID NO 5
<211> LENGTH: 9
<212> TYPE: PRT
<213> ORGANISM: Homo sapiens
<220> FEATURE:
<223> OTHER INFORMATION: heavy chain CDR3 for 10D1

<400> SEQUENCE: 5

Thr Gly Trp Leu Gly Pro Phe Asp Tyr
 1               5
```

-continued

```
<210> SEQ ID NO 6
<211> LENGTH: 12
<212> TYPE: PRT
<213> ORGANISM: Homo sapiens
<220> FEATURE:
<223> OTHER INFORMATION: light chain CDR1 for 10D1

<400> SEQUENCE: 6

Arg Ala Ser Gln Ser Val Gly Ser Ser Tyr Leu Ala
 1               5                  10

<210> SEQ ID NO 7
<211> LENGTH: 7
<212> TYPE: PRT
<213> ORGANISM: Homo sapiens
<220> FEATURE:
<223> OTHER INFORMATION: light chain CDR2 for 10D1

<400> SEQUENCE: 7

Gly Ala Phe Ser Arg Ala Thr
 1               5

<210> SEQ ID NO 8
<211> LENGTH: 9
<212> TYPE: PRT
<213> ORGANISM: Homo sapiens
<220> FEATURE:
<223> OTHER INFORMATION: light chain CDR3 for 10D1

<400> SEQUENCE: 8

Gln Gln Tyr Gly Ser Ser Pro Trp Thr
 1               5

<210> SEQ ID NO 9
<211> LENGTH: 118
<212> TYPE: PRT
<213> ORGANISM: Homo sapiens
<220> FEATURE:
<223> OTHER INFORMATION: heavy chain variable region sequence for 10D1

<400> SEQUENCE: 9

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
            20                  25                  30

Thr Met His Trp Val Arg Gln Ala Pro Gly Lys Gly Leu Glu Trp Val
        35                  40                  45

Thr Phe Ile Ser Tyr Asp Gly Asn Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ile Tyr Tyr Cys
                85                  90                  95

Ala Arg Thr Gly Trp Leu Gly Pro Phe Asp Tyr Trp Gly Gln Gly Thr
            100                 105                 110

Leu Val Thr Val Ser Ser
        115

<210> SEQ ID NO 10
<211> LENGTH: 108
<212> TYPE: PRT
<213> ORGANISM: Homo sapiens
<220> FEATURE:
<223> OTHER INFORMATION: light chain variable region sequence for 10D1
```

-continued

```
<400> SEQUENCE: 10

Glu Ile Val Leu Thr Gln Ser Pro Gly Thr Leu Ser Leu Ser Pro Gly
  1               5                  10                  15

Glu Arg Ala Thr Leu Ser Cys Arg Ala Ser Gln Ser Val Gly Ser Ser
             20                  25                  30

Tyr Leu Ala Trp Tyr Gln Gln Lys Pro Gly Gln Ala Pro Arg Leu Leu
         35                  40                  45

Ile Tyr Gly Ala Phe Ser Arg Ala Thr Gly Ile Pro Asp Arg Phe Ser
     50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Pro
                 85                  90                  95

Trp Thr Phe Gly Gln Gly Thr Lys Val Glu Ile Lys
             100                 105
```